United States Patent
Wang et al.

(10) Patent No.: US 10,077,308 B2
(45) Date of Patent: Sep. 18, 2018

(54) PD-L1 SPECIFIC MONOCLONAL ANTIBODIES FOR DISEASE TREATMENT AND DIAGNOSIS

(71) Applicants: AskGene Pharma Inc., Camarillo, CA (US); Jiangsu AoSaiKang Pharmaceutical Co., Ltd., Nanjing (CN)

(72) Inventors: Aijun Wang, Camarillo, CA (US); Kurt Shanebeck, Camarillo, CA (US); Donggou He, Camarillo, CA (US); Chen Yao, Moorpark, CA (US); Lu Li, Camarillo, CA (US); Fang Xia, Camarillo, CA (US); Yuefeng Lu, Newbury Park, CA (US); Jian-Feng Lu, Oak Park, CA (US); Lan Yang, Camarillo, CA (US)

(73) Assignees: AskGene Pharma Inc., Camarillo, CA (US); Jiangsu AoSaiKang Pharmaceutical Co., Ltd., Nanjing (CN)

(*) Notice: Subject to any disclaimer, the term of this patent is extended or adjusted under 35 U.S.C. 154(b) by 0 days.

(21) Appl. No.: 15/620,771

(22) Filed: Jun. 12, 2017

(65) Prior Publication Data
US 2017/0355770 A1  Dec. 14, 2017

Related U.S. Application Data

(60) Provisional application No. 62/349,640, filed on Jun. 13, 2016.

(51) Int. Cl.
*C07K 16/00* (2006.01)
*C07K 16/28* (2006.01)
*A61K 39/00* (2006.01)

(52) U.S. Cl.
CPC .... *C07K 16/2827* (2013.01); *A61K 2039/505* (2013.01); *C07K 2317/24* (2013.01); *C07K 2317/31* (2013.01); *C07K 2317/51* (2013.01); *C07K 2317/515* (2013.01); *C07K 2317/92* (2013.01)

(58) Field of Classification Search
None
See application file for complete search history.

(56) References Cited

U.S. PATENT DOCUMENTS

2014/0341917 A1  11/2014  Nastri et al.

FOREIGN PATENT DOCUMENTS

| WO | 2015048520 A1 | 4/2015 |
| WO | 2015061668 A1 | 4/2015 |
| WO | 2016000619 A1 | 1/2016 |
| WO | 2016022630 A1 | 2/2016 |

OTHER PUBLICATIONS

Rudikoff et al. (Proc Natl Acad Sci USA 1982 vol. 79 p. 1979) (Year: 1982).*
MacCallum et al. J. Mol. Biol. (1996) 262, 732-745 (Year: 1996).*
Pascalis et al. (The Journal of Immunology (2002) 169, 3076-3084) (Year: 2002).*
Casset et al. (BBRC 2003, 307:198-205) (Year: 2003).*
Vajdos et al. (J. Mol. Biol. (2002) 320, 415-428) (Year: 2002).*
Chen et al. (J. Mol. Bio. (1999) 293, 865-881) (Year: 1999).*
Wu et al. (J. Mol. Biol. (1999) 294, 151-162) (Year: 1999).*
Padlan et al. (PNAS 1989, 86:5938-5942) (Year: 1989).*
Lamminmaki et al. (JBC 2001, 276:36687-36694) (Year: 2001).*
White et al. (2001, Ann. Rev. Med., 2001, 52:125-145) (Year: 2001).*
Meibohm (Pharmacokinetics and Pharmacodynamics of Biotech Drugs, Wiley-VHC, 2006, chapter 3, p. 45-91) (Year: 2006).*
International Search Report and Written Opinion for PCT/US2017/037076 dated Oct. 27, 2017.

* cited by examiner

*Primary Examiner* — Laura B Goddard
*Assistant Examiner* — Meera Natarajan
(74) *Attorney, Agent, or Firm* — Entralta P.C.; James W. Collett; Peter D. Weinstein

(57) ABSTRACT

The present invention relates to compositions and methods for immunotherapy of a subject afflicted with diseases such as cancer, an infectious disease, or a neurodegenerative disease, which methods comprise administering to the subject a composition comprising a therapeutically effective amount of an anti-PD-L1 antibody or portion thereof that potentiates an endogenous immune response, either stimulating the activation of the endogenous response or inhibiting the suppression of the endogenous response.

14 Claims, 6 Drawing Sheets

Specification includes a Sequence Listing.

Figure 1A
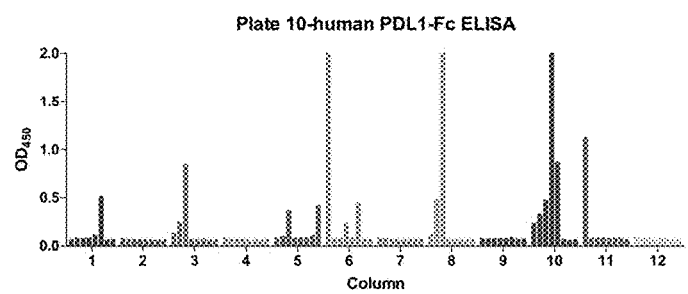
Figure 1B
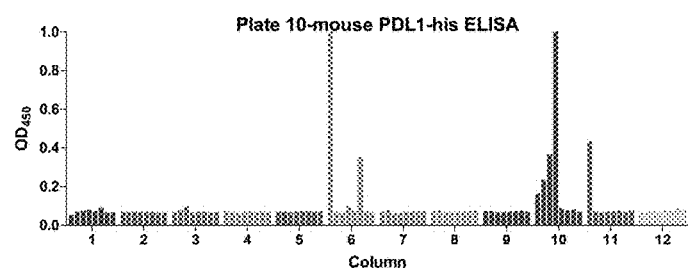
Figure 2A-C
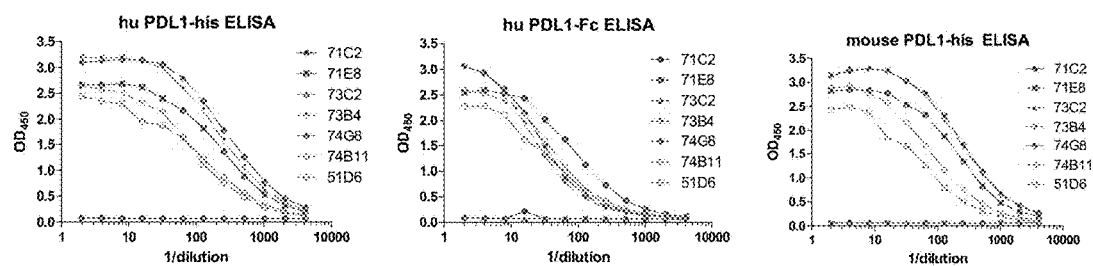

Figure 3A-B
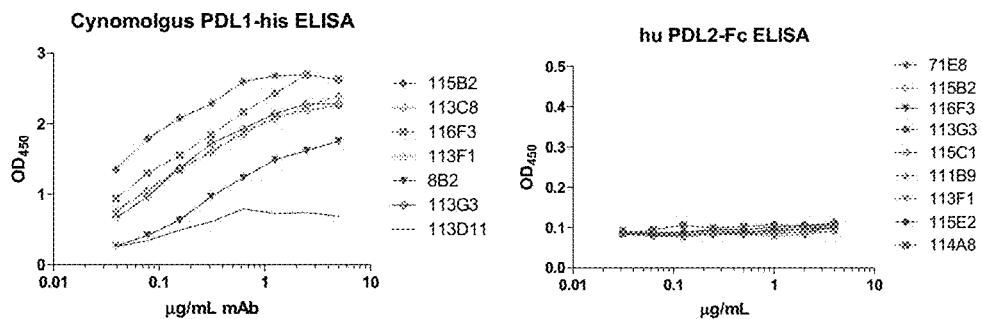
Figure 4
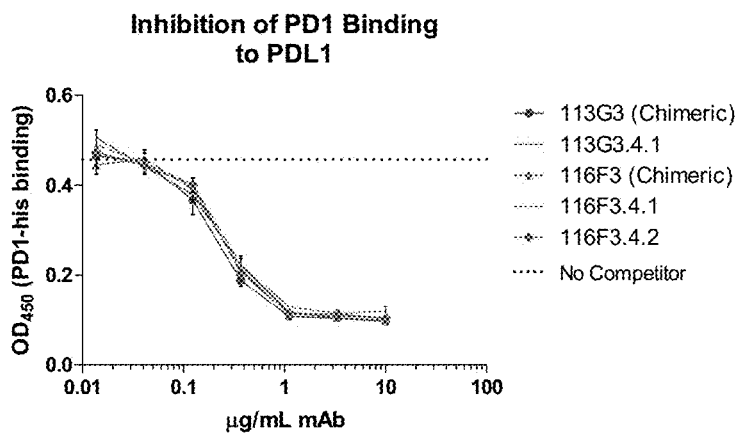
Figure 5
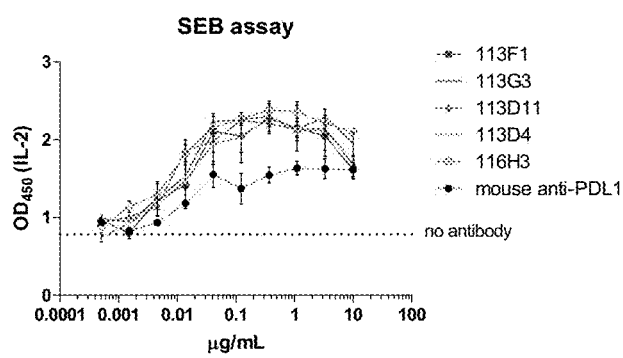

Green=hIgG
Red=113B2
Blue=17C1
Black=111C4
Purple=111F1

|  | Humanized | Chimeric | Anti-PDL1 Reference |
|---|---|---|---|
| EC50 | 0.03894 | 0.04828 | 0.04589 |

SEQUENCE LISTING

```
<160> NUMBER OF SEQ ID NOS: 115

<210> SEQ ID NO 1
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: Heavy chain variable domain

<400> SEQUENCE: 1

Cys Gln Ser Val Lys Glu Ser Glu Gly Gly Leu Phe Lys Pro Thr Asp
1               5                  10                  15

Thr Leu Thr Leu Thr Cys Thr Val Ser Gly Ile Asp Leu Asn Ser Ile
            20                  25                  30

Ala Ile Ser Trp Val Arg Gln Ala Pro Gly Asn Gly Leu Glu Trp Ile
        35                  40                  45

Gly Thr Ile Gly Ser Ser Gly Ser Ala Tyr Tyr Ala Ser Trp Ala Lys
    50                  55                  60

Ser Arg Ser Thr Ile Thr Arg Asn Thr Ser Glu Asn Thr Val Thr Leu
65                  70                  75                  80

Glu Met Thr Ser Leu Thr Ala Ala Asp Thr Ala Thr Tyr Phe Cys Ala
                85                  90                  95

Lys Glu Ile Leu Tyr Tyr Gly Met Asp Leu Trp Gly Pro Gly Thr Leu
            100                 105                 110
```

Val Thr Val Ser Ser
        115

<210> SEQ ID NO 2
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: Heavy chain variable domain

<400> SEQUENCE: 2

Cys Gln Ser Val Lys Glu Ser Glu Gly Gly Leu Phe Lys Pro Thr Asp
1               5                   10                  15

Thr Leu Thr Leu Thr Cys Lys Val Ser Gly Ile Asp Leu Ser Ser Ile
            20                  25                  30

Ser Ile Ser Trp Val Arg Gln Ala Pro Gly Asn Gly Leu Glu Trp Ile
        35                  40                  45

Gly Val Ile Asn Ser Tyr Gly Asn Thr Tyr Ala Ser Trp Ala Lys
    50                  55                  60

Ser Arg Ser Thr Ile Thr Arg Asn Thr Asn Glu Asn Thr Val Thr Leu
65                  70                  75                  80

Lys Met Thr Ser Leu Thr Ala Ala Asp Thr Ala Thr Tyr Phe Cys Ala
                85                  90                  95

Lys Glu Ile Leu Tyr Tyr Gly Met Asp Leu Trp Gly Pro Gly Thr Leu
            100                 105                 110

Val Thr Val Ser Ser
        115

<210> SEQ ID NO 3
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: Heavy chain variable region

<400> SEQUENCE: 3

Cys Gln Ser Val Lys Glu Ser Glu Gly Gly Leu Phe Lys Pro Met Asp
1               5                   10                  15

Thr Leu Thr Leu Thr Cys Thr Val Ser Gly Ile Asp Leu Gly Ser Val
            20                  25                  30

Ala Ile Ser Trp Val Arg Gln Ala Pro Gly Lys Gly Leu Glu Trp Ile
        35                  40                  45

Gly Thr Ile Gly Ser Ser Gly Ser Ala Tyr Tyr Ala Ser Trp Ala Lys
    50                  55                  60

Ser Arg Ser Thr Ile Thr Arg Asn Thr Asn Leu Asn Thr Val Thr Leu
65                  70                  75                  80

Lys Met Thr Ser Leu Thr Ala Ala Asp Thr Ala Ser Tyr Phe Cys Ala
                85                  90                  95

Lys Glu Ile Leu Tyr Tyr Gly Met Asp Arg Trp Gly Pro Gly Thr Leu
            100                 105                 110

Val Thr Val Ser Ser
        115

<210> SEQ ID NO 4
<211> LENGTH: 117
<212> TYPE: PRT
<213> ORGANISM: Oryctolagus cuniculus

```
<220> FEATURE:
<221> NAME/KEY: MISC_FEATURE
<223> OTHER INFORMATION: Heavy chain variable region

<400> SEQUENCE: 4

Cys Gln Ser Val Lys Glu Ser Glu Gly Gly Leu Phe Lys Pro Thr Asp
1               5                   10                  15

Thr Leu Thr Leu Thr Cys Thr Val Ser Gly Ile Asp Leu Ser Ser Ile
            20                  25                  30

Ser Ile Gly Trp Val Arg Gln Ala Pro Gly Asn Gly Leu Glu Trp Ile
        35                  40                  45

Gly Thr Ile Ser Asp Ser Gly Ser Ala Tyr Tyr Ala Ser Trp Ala Lys
    50                  55                  60

Ser Arg Ser Thr Ile Thr Arg Asn Thr Asn Glu Asn Thr Val Thr Leu
65                  70                  75                  80

Lys Met Thr Ser Leu Thr Ala Ala Asp Thr Ala Ser Tyr Phe Cys Ala
                85                  90                  95

Lys Glu Ile Leu Tyr Tyr Gly Met Asp Leu Trp Gly Pro Gly Thr Leu
            100                 105                 110

Val Thr Val Ser Ser
        115

<210> SEQ ID NO 5
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: Heavy chain variable region

<400> SEQUENCE: 5

Cys Gln Ser Val Lys Glu Ser Glu Gly Gly Leu Phe Lys Pro Thr Asp
1               5                   10                  15

Thr Leu Thr Leu Thr Cys Thr Val Ser Gly Ile Asp Leu Ser Ser Ile
            20                  25                  30

Ala Ile Ser Trp Val Arg Gln Ala Pro Gly Asn Gly Leu Glu Trp Ile
        35                  40                  45

Gly Thr Ile Asn Ser Tyr Gly Ser Thr Tyr Tyr Ala Ser Trp Ala Gln
    50                  55                  60

Ser Arg Ser Thr Ile Thr Arg Asn Thr Asn Glu Asn Thr Val Thr Leu
65                  70                  75                  80

Lys Met Thr Ser Leu Thr Ala Ala Asp Thr Ala Ser Tyr Phe Cys Ala
                85                  90                  95

Lys Glu Ile Leu Tyr Tyr Gly Met Asp Val Trp Gly Pro Gly Thr Leu
            100                 105                 110

Val Thr Val Ser Ser
        115

<210> SEQ ID NO 6
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: Heavy chain variable region
<220> FEATURE:
<221> NAME/KEY: misc_feature
<222> LOCATION: (8)..(8)
<223> OTHER INFORMATION: Xaa can be any naturally occurring amino acid

<400> SEQUENCE: 6
```

Cys Gln Ser Val Lys Glu Ser Xaa Gly Gly Leu Phe Lys Pro Thr Asp
1               5                   10                  15

Thr Leu Thr Leu Thr Cys Thr Val Ser Gly Phe Ser Leu Ser Ser Val
            20                  25                  30

Ala Val Ser Trp Val Arg Gln Ala Pro Gly Asn Gly Leu Glu Trp Ile
        35                  40                  45

Gly Thr Ile Ser Tyr Thr Gly Thr Thr Tyr Tyr Ala Ser Trp Ala Lys
    50                  55                  60

Ser Arg Ser Thr Ile Thr Arg Asn Thr Asp Glu Asn Thr Val Thr Leu
65              70                  75                  80

Lys Met Pro Ser Leu Thr Val Ala Asp Thr Ala Thr Tyr Phe Cys Ala
            85                  90                  95

Lys Glu Ile Leu Tyr Tyr Gly Met Asp Phe Trp Gly Pro Gly Thr Leu
            100                 105                 110

Val Thr Val Ser Ser
        115

<210> SEQ ID NO 7
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: Heavy chain variable region

<400> SEQUENCE: 7

Cys Gln Ser Val Lys Glu Ser Glu Gly Gly Leu Phe Lys Pro Thr Asp
1               5                   10                  15

Thr Leu Thr Leu Thr Cys Thr Val Ser Gly Phe Ser Leu Ser Ser Val
            20                  25                  30

Ala Val Ser Trp Val Arg Gln Ala Pro Gly Lys Gly Leu Glu Trp Ile
        35                  40                  45

Gly Thr Ile Ser Tyr Thr Gly Asn Thr Tyr Tyr Ala Ser Trp Ala Lys
    50                  55                  60

Ser Arg Ser Thr Ile Thr Arg Asn Thr Asn Glu Asn Thr Val Thr Leu
65              70                  75                  80

Lys Met Pro Ser Leu Thr Val Ala Asp Thr Ala Thr Tyr Phe Cys Ala
            85                  90                  95

Lys Glu Ile Leu Tyr Tyr Gly Met Asp Phe Trp Gly Pro Gly Thr Leu
            100                 105                 110

Val Thr Val Ser Ser
        115

<210> SEQ ID NO 8
<211> LENGTH: 122
<212> TYPE: PRT
<213> ORGANISM: Oryctolagus cuniculus
<220> FEATURE:
<221> NAME/KEY: MISC_FEATURE
<223> OTHER INFORMATION: Heavy chain variable region

<400> SEQUENCE: 8

Cys Gln Glu Gln Leu Val Glu Ser Gly Gly Leu Val Gln Pro Gly
1               5                   10                  15

Gly Thr Leu Lys Leu Ser Cys Lys Gly Ser Gly Phe Asp Leu Ser Ser
            20                  25                  30

Asn Ala Met Cys Trp Val Arg Gln Ala Pro Gly Lys Gly Leu Glu Trp
        35                  40                  45

```
Ile Gly Cys Ile Val Tyr Gly Asn Cys Tyr Tyr Ala Ser Trp Val Asn
        50                  55                  60

Gly Arg Phe Thr Ile Ser Ser Asp Asn Ala Gln Ser Val Asp Leu
65                  70                  75                  80

Gln Leu Asn Ser Leu Thr Ala Ala Asp Thr Ala Thr Tyr Phe Cys Ala
                85                  90                  95

Arg Asp Pro Ala Gly Ser Ser Val Tyr Thr Gly Gly Phe Asn Ile Trp
            100                 105                 110

Gly Pro Gly Thr Leu Val Thr Val Ser Ser
            115                 120
```

<210> SEQ ID NO 9
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: Heavy chain variable region

<400> SEQUENCE: 9

```
Cys Gln Ser Val Lys Glu Ser Glu Gly Gly Leu Phe Lys Pro Thr Asp
1               5                   10                  15

Thr Leu Thr Leu Thr Cys Thr Val Ser Gly Ile Asp Leu Ser Ser Val
                20                  25                  30

Ser Ile Ser Trp Val Arg Gln Ala Pro Gly Asn Gly Leu Glu Trp Ile
            35                  40                  45

Gly Thr Ile Gly Ala Ser Gly Ser Ala Tyr Tyr Ala Ser Trp Ala Lys
        50                  55                  60

Arg Arg Ser Thr Ile Thr Arg Asn Thr Asn Leu Asn Thr Val Thr Leu
65                  70                  75                  80

Lys Met Thr Ser Leu Thr Ala Ala Asp Thr Ala Ser Tyr Phe Cys Ala
                85                  90                  95

Lys Glu Ile Leu Tyr Tyr Gly Met Asp Leu Trp Gly Pro Gly Thr Leu
            100                 105                 110

Val Thr Val Ser Ser
        115
```

<210> SEQ ID NO 10
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: Light chain variable region

<400> SEQUENCE: 10

```
Cys Gln Ser Val Lys Glu Ser Glu Gly Gly Leu Phe Lys Pro Thr Asp
1               5                   10                  15

Thr Leu Thr Leu Thr Cys Thr Val Ser Gly Ile Asp Leu Ser Ser Val
                20                  25                  30

Ser Ile Ser Trp Val Arg Gln Ala Pro Gly Asn Gly Leu Glu Trp Ile
            35                  40                  45

Gly Thr Ile Gly Ala Ser Gly Ser Ala Tyr Tyr Ala Ser Trp Ala Lys
        50                  55                  60

Arg Arg Ser Thr Ile Thr Arg Asn Thr Asn Leu Asn Thr Val Thr Leu
65                  70                  75                  80

Lys Met Thr Ser Leu Thr Ala Ala Asp Thr Ala Ser Tyr Phe Cys Ala
                85                  90                  95
```

```
Lys Glu Ile Leu Tyr Tyr Gly Met Asp Leu Trp Gly Pro Gly Thr Leu
            100                 105                 110

Val Thr Val Ser Ser
        115

<210> SEQ ID NO 11
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: Light chain variable region

<400> SEQUENCE: 11

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Phe Ser Trp Tyr Gln Gln Lys Pro Gly Gln Arg Pro Lys Leu Leu Ile
        35                  40                  45

Tyr Asp Ala Ser Asn Leu Glu Ser Gly Val Pro Ser Arg Phe Lys Gly
    50                  55                  60

Ser Arg Ser Gly Thr Glu Tyr Thr Leu Thr Ile Ser Asp Leu Glu Trp
65                  70                  75                  80

Asp Asp Ala Ala Thr Tyr Tyr Cys Gln Cys Thr Tyr Gly Ser Thr Ser
                85                  90                  95

Ser Ser Asn Tyr Gly Asn Asn Phe Gly Gly Gly Thr Lys Val Val Val
            100                 105                 110

Val Arg Thr
        115

<210> SEQ ID NO 12
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: Light chain variable region

<400> SEQUENCE: 12

Asp Val Val Met Thr Gln Thr Pro Ala Ser Val Glu Ala Ser Val Gly
1               5                   10                  15

Gly Thr Val Thr Ile Asn Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Asn Leu Glu Pro Gly Val Pro Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ala Thr Tyr Gly Ser Thr Ser
                85                  90                  95

Ser Ser Asp Tyr Gly Asn Ala Phe Gly Gly Gly Thr Lys Val Val Val
            100                 105                 110

Val Arg Thr
        115

<210> SEQ ID NO 13
```

<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: Lifgt chain variable region

<400> SEQUENCE: 13

Asp Val Val Met Thr Gln Thr Pro Ala Ser Val Ser Gly Ala Val Gly
1               5                   10                  15

Gly Thr Val Thr Ile Lys Cys Gln Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Asn Leu Glu Pro Gly Val Pro Ser Arg Phe Lys Gly
    50                  55                  60

Ser Arg Ser Gly Thr Glu Tyr Thr Leu Thr Ile Thr Asp Leu Glu Cys
65                  70                  75                  80

Asp Asp Ala Ala Thr Tyr His Cys Gln Ala Thr Tyr Gly Ser Thr Ser
                85                  90                  95

Ser Ser Asp Tyr Gly Asn Ala Phe Gly Gly Gly Thr Lys Val Val Val
                100                 105                 110

Val Arg Thr
        115

<210> SEQ ID NO 14
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: Light chain variable region

<400> SEQUENCE: 14

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
            20                  25                  30

Leu Ala Trp Tyr Gln Gln Lys Pro Gly Gln Pro Pro Lys Leu Leu Ile
        35                  40                  45

Tyr Ala Ala Ser Asn Leu Glu Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Ser Thr Tyr Gly Thr Thr Ser
                85                  90                  95

Thr Ser Asp Tyr Gly Asn Ala Phe Gly Gly Gly Thr Lys Val Val Val
                100                 105                 110

Val Arg Thr
        115

<210> SEQ ID NO 15
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: Light chain varialble region

<400> SEQUENCE: 15

-continued

```
Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
            35                  40                  45

Tyr Ala Ala Ser Asn Leu Glu Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Ser Thr Tyr Gly Thr Thr Ser
                85                  90                  95

Thr Ser Asp Tyr Gly Asn Ala Phe Gly Gly Gly Thr Lys Val Val Val
                100                 105                 110

Val Arg Thr
        115
```

<210> SEQ ID NO 16
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: Light chain variable region

<400> SEQUENCE: 16

```
Asp Ile Val Met Thr Gln Thr Pro Ser Ser Val Ser Ala Ala Val Gly
1               5                   10                  15

Gly Thr Val Thr Ile Asn Cys Gln Ala Ser Gln Ser Ile Ser Ser Tyr
                20                  25                  30

Leu Ala Trp Tyr Gln Gln Lys Pro Gly Gln Pro Pro Lys Leu Leu Ile
            35                  40                  45

Tyr Gly Ala Ser Asn Leu Glu Ser Gly Val Pro Ser Arg Phe Lys Gly
    50                  55                  60

Ser Gly Ser Gly Thr Asp Phe Thr Leu Thr Ile Ser Asp Leu Glu Cys
65                  70                  75                  80

Ala Asp Ala Ala Thr Tyr Tyr Cys Gln Ser Thr Tyr Gly Ser Thr Ser
                85                  90                  95

Thr Ser Asp Tyr Gly Asn Ala Phe Gly Gly Gly Thr Lys Val Val Val
                100                 105                 110

Val Arg Thr
        115
```

<210> SEQ ID NO 17
<211> LENGTH: 112
<212> TYPE: PRT
<213> ORGANISM: Oryctolagus cuniculus
<220> FEATURE:
<221> NAME/KEY: MISC_FEATURE
<223> OTHER INFORMATION: Light chain variable region

<400> SEQUENCE: 17

```
Ala Ile Asp Met Thr Gln Thr Pro Ser Pro Val Ser Ala Ala Val Gly
1               5                   10                  15

Asp Thr Val Thr Ile Asn Cys Gln Ala Ser Glu Asn Ile Tyr Ser Phe
                20                  25                  30

Leu Ala Trp Tyr Gln Gln Lys Pro Gly His Ser Pro Lys Pro Leu Ile
            35                  40                  45
```

```
Tyr Phe Ala Ser Lys Leu Ala Ser Gly Val Pro Ser Arg Phe Lys Gly
    50                  55                  60

Ser Gly Ser Gly Thr Gln Phe Thr Leu Thr Ile Ser Asp Val Gln Cys
65                  70                  75                  80

Asp Asp Ala Ala Thr Tyr Tyr Cys Gln Gln Thr Val Ser Tyr Lys Asn
                85                  90                  95

Ala Asp Thr Ala Phe Gly Gly Gly Thr Lys Val Val Val Arg Thr
            100                 105                 110
```

<210> SEQ ID NO 18
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: Light chain variable region

<400> SEQUENCE: 18

```
Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Ser Asn Tyr
                20                  25                  30

Leu Ala Trp Tyr Gln Gln Lys Pro Gly Gln Arg Pro Lys Leu Leu Ile
            35                  40                  45

Tyr Ala Ala Ser Asn Leu Glu Pro Gly Val Pro Ser Arg Phe Lys Gly
    50                  55                  60

Ser Gly Ser Gly Thr Glu Tyr Thr Leu Thr Ile Thr Asp Leu Glu Cys
65                  70                  75                  80

Asp Asp Ala Ala Thr Tyr His Cys Gln Cys Thr Tyr Gly Ser Thr Ser
                85                  90                  95

Ser Ser Asp Tyr Gly Asn Ala Phe Gly Gly Gly Thr Lys Val Val Val
            100                 105                 110

Val Arg Thr
    115
```

<210> SEQ ID NO 19
<211> LENGTH: 6
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 19

```
Ser Ser Ile Ser Ile Gly
1               5
```

<210> SEQ ID NO 20
<211> LENGTH: 16
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 20

```
Thr Ile Ser Asp Ser Gly Ser Ala Tyr Tyr Ala Ser Trp Ala Lys Ser
1               5                   10                  15
```

<210> SEQ ID NO 21
<211> LENGTH: 9
<212> TYPE: PRT

-continued

<213> ORGANISM: Oryctolagus cuniculus
<220> FEATURE:
<221> NAME/KEY: MISC_FEATURE
<223> OTHER INFORMATION: CDR

<400> SEQUENCE: 21

Glu Ile Leu Tyr Tyr Gly Met Asp Leu
1               5

<210> SEQ ID NO 22
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 22

Gln Ala Ser Glu Asp Ile Glu Ser Tyr Leu Ala
1               5                   10

<210> SEQ ID NO 23
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 23

Ala Ala Ser Asn Leu Glu Pro
1               5

<210> SEQ ID NO 24
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 24

Gln Ala Thr Tyr Gly Ser Thr Ser Ser Ser Asp Tyr Gly Asn Ala
1               5                   10                  15

<210> SEQ ID NO 25
<211> LENGTH: 6
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 25

Ser Ser Val Ala Val Ser
1               5

<210> SEQ ID NO 26
<211> LENGTH: 16
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 26

Thr Ile Ser Tyr Thr Gly Thr Thr Tyr Tyr Ala Ser Trp Ala Lys Ser
1               5                   10                  15

```
<210> SEQ ID NO 27
<211> LENGTH: 9
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 27

Glu Ile Leu Tyr Tyr Gly Met Asp Phe
 1               5

<210> SEQ ID NO 28
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 28

Gln Ala Ser Gln Ser Val Ser Asn Leu Leu Val
 1               5                  10

<210> SEQ ID NO 29
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 29

Gly Ala Ser Asn Leu Glu Ser
 1               5

<210> SEQ ID NO 30
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 30

Gln Ser Thr Tyr Gly Ser Thr Ser Thr Ser Asp Tyr Gly Asn Ala
 1               5                  10                  15

<210> SEQ ID NO 31
<211> LENGTH: 6
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 31

Ser Ser Val Ala Val Ser
 1               5

<210> SEQ ID NO 32
<211> LENGTH: 16
<212> TYPE: PRT
<213> ORGANISM: Oryctolagus cuniculus
<220> FEATURE:
<221> NAME/KEY: MISC_FEATURE
<223> OTHER INFORMATION: CDR
```

<400> SEQUENCE: 32

Thr Ile Ser Tyr Thr Gly Asn Thr Tyr Tyr Ala Ser Trp Ala Lys Ser
1               5                   10                  15

<210> SEQ ID NO 33
<211> LENGTH: 9
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 33

Glu Ile Leu Tyr Tyr Gly Met Asp Phe
1               5

<210> SEQ ID NO 34
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 34

Gln Ala Ser Gln Ser Ile Ser Ser Tyr Leu Ala
1               5                   10

<210> SEQ ID NO 35
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 35

Gly Ala Ser Asn Leu Glu Ser
1               5

<210> SEQ ID NO 36
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 36

Gln Ser Thr Tyr Gly Ser Thr Ser Ser Asp Tyr Gly Asn Ala
1               5                   10                  15

<210> SEQ ID NO 37
<211> LENGTH: 6
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 37

Ser Ser Ile Ser Ile Ser
1               5

<210> SEQ ID NO 38
<211> LENGTH: 16

```
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 38

Val Ile Asn Ser Tyr Gly Asn Thr Tyr Tyr Ala Ser Trp Ala Lys Ser
1               5                   10                  15

<210> SEQ ID NO 39
<211> LENGTH: 9
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 39

Glu Ile Leu Tyr Tyr Gly Met Asp Leu
1               5

<210> SEQ ID NO 40
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 40

Gln Ala Ser Gln Ser Ile Ser Ser Tyr Phe Ser
1               5                   10

<210> SEQ ID NO 41
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 41

Asp Ala Ser Asn Leu Glu Ser
1               5

<210> SEQ ID NO 42
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 42

Gln Cys Thr Tyr Gly Ser Thr Ser Ser Asn Tyr Gly Asn Asn
1               5                   10                  15

<210> SEQ ID NO 43
<211> LENGTH: 6
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 43

Ser Ser Ile Ala Ile Ser
1               5
```

<210> SEQ ID NO 44
<211> LENGTH: 16
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 44

Thr Ile Asn Ser Tyr Gly Ser Thr Tyr Tyr Ala Ser Trp Ala Gln Ser
1               5                   10                  15

<210> SEQ ID NO 45
<211> LENGTH: 9
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 45

Glu Ile Leu Tyr Tyr Gly Met Asp Val
1               5

<210> SEQ ID NO 46
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 46

Gln Ala Ser Gln Ser Ile Ser Ser Tyr Leu Ala
1               5                   10

<210> SEQ ID NO 47
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 47

Ala Ala Ser Asn Leu Glu Ser
1               5

<210> SEQ ID NO 48
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 48

Gln Ser Thr Tyr Gly Thr Thr Ser Thr Ser Asp Tyr Gly Asn Ala
1               5                   10                  15

<210> SEQ ID NO 49
<211> LENGTH: 6
<212> TYPE: PRT
<213> ORGANISM: Oryctolagus cuniculus
<220> FEATURE:
<221> NAME/KEY: MISC_FEATURE

<223> OTHER INFORMATION: CDR

<400> SEQUENCE: 49

Asn Ser Ile Ala Ile Ser
1               5

<210> SEQ ID NO 50
<211> LENGTH: 16
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 50

Thr Ile Gly Ser Ser Gly Ser Ala Tyr Tyr Ala Ser Trp Ala Lys Ser
1               5                   10                  15

<210> SEQ ID NO 51
<211> LENGTH: 9
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 51

Glu Ile Leu Tyr Tyr Gly Met Asp Leu
1               5

<210> SEQ ID NO 52
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 52

Gln Ala Ser Gln Ser Ile Ser Ser Tyr Leu Ala
1               5                   10

<210> SEQ ID NO 53
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 53

Ala Ala Ser Asn Val Glu Pro
1               5

<210> SEQ ID NO 54
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 54

Gln Ser Thr Tyr Gly Ser Thr Gly Gly Gly Asp Tyr Gly Asn Ala
1               5                   10                  15

<210> SEQ ID NO 55

```
<211> LENGTH: 6
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 55

Gly Ser Val Ala Ile Ser
1               5

<210> SEQ ID NO 56
<211> LENGTH: 16
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 56

Thr Ile Gly Ser Ser Gly Ser Ala Tyr Tyr Ala Ser Trp Ala Lys Ser
1               5                   10                  15

<210> SEQ ID NO 57
<211> LENGTH: 9
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 57

Glu Ile Leu Tyr Tyr Gly Met Asp Arg
1               5

<210> SEQ ID NO 58
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 58

Gln Ala Ser Gln Ser Ile Ser Ser Tyr Leu Ala
1               5                   10

<210> SEQ ID NO 59
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 59

Ala Ala Ser Asn Leu Glu Pro
1               5

<210> SEQ ID NO 60
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 60
```

```
Gln Ala Thr Tyr Gly Ser Thr Ser Ser Ser Asp Tyr Gly Asn Ala
1               5                   10                  15

<210> SEQ ID NO 61
<211> LENGTH: 5
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 61

Ser Asn Ala Met Cys
1               5

<210> SEQ ID NO 62
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 62

Cys Ile Val Tyr Gly Asn Cys Tyr Tyr Ala Ser Trp Val Asn Gly
1               5                   10                  15

<210> SEQ ID NO 63
<211> LENGTH: 14
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 63

Asp Pro Ala Gly Ser Ser Val Tyr Thr Gly Gly Phe Asn Ile
1               5                   10

<210> SEQ ID NO 64
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 64

Gln Ala Ser Glu Asn Ile Tyr Ser Phe Leu Ala
1               5                   10

<210> SEQ ID NO 65
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 65

Phe Ala Ser Lys Leu Ala Ser
1               5

<210> SEQ ID NO 66
<211> LENGTH: 12
<212> TYPE: PRT
<213> ORGANISM: Oryctolagus cuniculus
<220> FEATURE:
```

```
<221> NAME/KEY: MISC_FEATURE
<223> OTHER INFORMATION: CDR

<400> SEQUENCE: 66

Gln Gln Thr Val Ser Tyr Lys Asn Ala Asp Thr Ala
1               5                   10

<210> SEQ ID NO 67
<211> LENGTH: 6
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 67

Ser Ser Val Ser Ile Ser
1               5

<210> SEQ ID NO 68
<211> LENGTH: 16
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 68

Thr Ile Gly Ala Ser Gly Ser Ala Tyr Tyr Ala Ser Trp Ala Lys Arg
1               5                   10                  15

<210> SEQ ID NO 69
<211> LENGTH: 9
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 69

Glu Ile Leu Tyr Tyr Gly Met Asp Leu
1               5

<210> SEQ ID NO 70
<211> LENGTH: 11
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 70

Gln Ala Ser Gln Ser Ile Ser Asn Tyr Leu Ala
1               5                   10

<210> SEQ ID NO 71
<211> LENGTH: 7
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 71

Ala Ala Ser Asn Leu Glu Pro
1               5
```

```
<210> SEQ ID NO 72
<211> LENGTH: 15
<212> TYPE: PRT
<213> ORGANISM: Oryctolagus cuniculus
<220> FEATURE:
<221> NAME/KEY: MISC_FEATURE
<223> OTHER INFORMATION: CDR

<400> SEQUENCE: 72

Gln Cys Thr Tyr Gly Ser Thr Ser Ser Asp Tyr Gly Asn Ala
1               5                   10                  15

<210> SEQ ID NO 73
<211> LENGTH: 119
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Ser Ile
            20                  25                  30

Ser Ile Gly Trp Ile Arg Gln Pro Pro Gly Lys Gly Leu Glu Trp Ile
        35                  40                  45

Gly Thr Ile Ser Asp Ser Gly Ser Ala Tyr Tyr Ala Ser Trp Ala Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ile Leu Tyr Tyr Gly Met Asp Leu Trp Gly Gln Gly Thr Leu
            100                 105                 110

Val Thr Val Ser Ser Ala Ser
        115

<210> SEQ ID NO 74
<211> LENGTH: 119
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 74

Gln Val Gln Leu Gln Glu Ser Gly Pro Gly Leu Val Lys Pro Ser Glu
1               5                   10                  15

Thr Leu Ser Leu Thr Cys Thr Val Ser Gly Ile Asp Leu Ser Ser Ile
            20                  25                  30

Ser Ile Gly Trp Ile Arg Gln Pro Pro Gly Lys Gly Leu Glu Trp Ile
        35                  40                  45

Gly Thr Ile Ser Asp Ser Gly Ser Ala Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ile Leu Tyr Tyr Gly Met Asp Leu Trp Gly Gln Gly Thr Leu
            100                 105                 110
```

Val Thr Val Ser Ser Ala Ser
        115

<210> SEQ ID NO 75
<211> LENGTH: 119
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 75

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Ser Ser Ile
            20                  25                  30

Ser Ile Gly Trp Ile Arg Gln Pro Pro Gly Lys Gly Leu Glu Trp Ile
        35                  40                  45

Gly Thr Ile Ser Asp Ser Gly Ser Ala Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ile Leu Tyr Tyr Gly Met Asp Leu Trp Gly Gln Gly Thr Leu
            100                 105                 110

Val Thr Val Ser Ser Ala Ser
        115

<210> SEQ ID NO 76
<211> LENGTH: 119
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Thr Val Ser Gly Phe Thr Leu Ser Ser Ile
            20                  25                  30

Ser Ile Gly Trp Val Arg Gln Ala Pro Gly Lys Gly Leu Glu Trp Val
        35                  40                  45

Ser Thr Ile Ser Asp Ser Gly Ser Ala Tyr Tyr Ala Ser Trp Ala Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Glu Ile Leu Tyr Tyr Gly Met Asp Leu Trp Gly Gln Gly Thr Leu
            100                 105                 110

Val Thr Val Ser Ser Ala Ser
        115

<210> SEQ ID NO 77
<211> LENGTH: 119
<212> TYPE: PRT
<213> ORGANISM: Oryctolagus cuniculus

<220> FEATURE:
<221> NAME/KEY: MISC_FEATURE
<223> OTHER INFORMATION: VH

<400> SEQUENCE: 77

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Leu Ser Ser Ile
            20                  25                  30

Ser Ile Gly Trp Val Arg Gln Ala Pro Gly Lys Gly Leu Glu Trp Val
        35                  40                  45

Ser Thr Ile Ser Asp Ser Gly Ser Ala Tyr Tyr Ala Ser Trp Ala Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Glu Ile Leu Tyr Tyr Gly Met Asp Leu Trp Gly Gln Gly Thr Leu
            100                 105                 110

Val Thr Val Ser Ser Ala Ser
        115
```

<210> SEQ ID NO 78
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 78

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Glu Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Thr Tyr Gly Ser Thr Ser
                85                  90                  95

Ser Ser Asp Tyr Gly Asn Ala Phe Gly Gly Gly Thr Lys Val Glu Ile
            100                 105                 110

Lys Arg Thr
        115
```

<210> SEQ ID NO 79
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 79

```
Asp Ile Gln Met Thr Gln Ser Pro Ser Ser Leu Ser Ala Ser Val Gly
 1               5                  10                  15
```

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Glu Pro Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Ala Thr Tyr Gly Ser Thr Ser
                85                  90                  95

Ser Ser Asp Tyr Gly Asn Ala Phe Gly Gly Gly Thr Lys Val Glu Ile
            100                 105                 110

Lys Arg Thr
        115

<210> SEQ ID NO 80
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Thr Val Ser Gly Phe Ser Leu Ser Ser Val
            20                  25                  30

Ala Val Ser Trp Val Arg Gln Ala Pro Gly Lys Gly Leu Glu Trp Val
        35                  40                  45

Ser Thr Ile Ser Tyr Thr Gly Thr Thr Tyr Tyr Ala Ser Trp Ala Lys
50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Glu Ile Leu Tyr Tyr Gly Met Asp Phe Trp Gly Gln Gly Thr Leu
            100                 105                 110

Val Thr Val Ser Ser
        115

<210> SEQ ID NO 81
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Leu Ser Ser Val
            20                  25                  30

Ala Val Ser Trp Val Arg Gln Ala Pro Gly Lys Gly Leu Glu Trp Val
        35                  40                  45

Ser Thr Ile Ser Tyr Thr Gly Thr Thr Tyr Tyr Ala Ser Trp Ala Lys
50                  55                  60

```
Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Lys Glu Ile Leu Tyr Tyr Gly Met Asp Phe Trp Gly Gln Gly Thr Leu
            100                 105                 110

Val Thr Val Ser Ser
            115

<210> SEQ ID NO 82
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 82

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Leu Ser Ser Val
             20                  25                  30

Ala Val Ser Trp Ile Arg Gln Pro Pro Gly Lys Gly Leu Glu Trp Ile
             35                  40                  45

Gly Thr Ile Ser Tyr Thr Gly Thr Thr Tyr Tyr Ala Ser Trp Ala Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
             85                  90                  95

Lys Glu Ile Leu Tyr Tyr Gly Met Asp Phe Trp Gly Gln Gly Thr Leu
            100                 105                 110

Val Thr Val Ser Ser
            115

<210> SEQ ID NO 83
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 83

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Leu Ser Ser Val
             20                  25                  30

Ala Val Ser Trp Ile Arg Gln Pro Pro Gly Lys Gly Leu Glu Trp Ile
             35                  40                  45

Gly Thr Ile Ser Tyr Thr Gly Thr Thr Tyr Tyr Ala Ser Trp Ala Lys
 50                  55                  60

Ser Arg Val Thr Ile Ser Arg Asp Thr Ser Lys Asn Gln Phe Ser Leu
 65                  70                  75                  80

Lys Leu Ser Ser Val Thr Ala Ala Asp Thr Ala Val Tyr Tyr Cys Ala
             85                  90                  95

Lys Glu Ile Leu Tyr Tyr Gly Met Asp Phe Trp Gly Gln Gly Thr Leu
            100                 105                 110
```

Val Thr Val Ser Ser
        115

<210> SEQ ID NO 84
<211> LENGTH: 117
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 84

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Ser Val
            20                  25                  30

Ala Val Ser Trp Ile Arg Gln Pro Pro Gly Lys Gly Leu Glu Trp Ile
        35                  40                  45

Gly Thr Ile Ser Tyr Thr Gly Thr Thr Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Glu Ile Leu Tyr Tyr Gly Met Asp Phe Trp Gly Gln Gly Thr Leu
            100                 105                 110

Val Thr Val Ser Ser
        115

<210> SEQ ID NO 85
<211> LENGTH: 113
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Val Ser Asn Leu
            20                  25                  30

Leu Val Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Gly Ser Thr Ser
                85                  90                  95

Thr Ser Asp Tyr Gly Asn Ala Phe Gly Gly Gly Thr Lys Val Glu Ile
            100                 105                 110

Lys

<210> SEQ ID NO 86
<211> LENGTH: 123
<212> TYPE: PRT
<213> ORGANISM: Oryctolagus cuniculus
<220> FEATURE:
<221> NAME/KEY: MISC_FEATURE

<223> OTHER INFORMATION: VH

<400> SEQUENCE: 86

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Asn
            20                  25                  30

Ala Met Cys Trp Val Arg Gln Ala Pro Gly Lys Gly Leu Glu Trp Ile
        35                  40                  45

Gly Cys Ile Val Tyr Gly Asn Cys Tyr Tyr Ala Ser Trp Val Asn Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Pro Ala Gly Ser Ser Val Tyr Thr Gly Gly Phe Asn Ile Trp Gly
            100                 105                 110

Gln Gly Thr Leu Val Thr Val Ser Ser Ala Ser
        115                 120

<210> SEQ ID NO 87
<211> LENGTH: 123
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Asn
            20                  25                  30

Ala Met Cys Trp Val Arg Gln Ala Pro Gly Lys Gly Leu Glu Trp Ile
        35                  40                  45

Gly Cys Ile Val Tyr Gly Asn Cys Tyr Tyr Ala Ser Trp Val Asn Gly
    50                  55                  60

Arg Phe Thr Ile Ser Ser Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Pro Ala Gly Ser Ser Val Tyr Thr Gly Gly Phe Asn Ile Trp Gly
            100                 105                 110

Gln Gly Thr Leu Val Thr Val Ser Ser Ala Ser
        115                 120

<210> SEQ ID NO 88
<211> LENGTH: 123
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Asn
            20                  25                  30

```
Ala Met Ser Trp Val Arg Gln Ala Pro Gly Lys Gly Leu Glu Trp Ile
        35                  40                  45

Gly Cys Ile Val Tyr Gly Asn Cys Tyr Tyr Ala Ser Trp Val Asn Gly
    50                  55                  60

Arg Phe Thr Ile Ser Ser Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Pro Ala Gly Ser Ser Val Tyr Thr Gly Gly Phe Asn Ile Trp Gly
            100                 105                 110

Gln Gly Thr Leu Val Thr Val Ser Ser Ala Ser
        115                 120
```

<210> SEQ ID NO 89
<211> LENGTH: 123
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 89

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Ser Asn
            20                  25                  30

Ala Met Ser Trp Val Arg Gln Ala Pro Gly Lys Gly Leu Glu Trp Ile
        35                  40                  45

Gly Ser Ile Val Tyr Gly Asn Ser Tyr Tyr Ala Ser Trp Val Asn Gly
    50                  55                  60

Arg Phe Thr Ile Ser Ser Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Asp Pro Ala Gly Ser Ser Val Tyr Thr Gly Gly Phe Asn Ile Trp Gly
            100                 105                 110

Gln Gly Thr Leu Val Thr Val Ser Ser Ala Ser
        115                 120
```

<210> SEQ ID NO 90
<211> LENGTH: 112
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 90

```
Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Phe Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Asp Asp Phe Ala Thr Tyr Tyr Cys Gln Gln Thr Val Ser Tyr Lys Asn
                85                  90                  95

Ala Asp Thr Ala Phe Gly Gly Gly Thr Lys Val Glu Ile Lys Arg Thr
            100                 105                 110

<210> SEQ ID NO 91
<211> LENGTH: 112
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 91

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Phe Ala Ser Lys Leu Ala Ser Gly Val Pro Ser Arg Phe Lys Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Thr Val Ser Tyr Lys Asn
                85                  90                  95

Ala Asp Thr Ala Phe Gly Gly Gly Thr Lys Val Glu Ile Lys Arg Thr
            100                 105                 110

<210> SEQ ID NO 92
<211> LENGTH: 112
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 92

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Phe Ala Ser Lys Leu Ala Ser Gly Val Pro Ser Arg Phe Ser Gly
50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Gln Thr Val Ser Tyr Lys Asn
                85                  90                  95

Ala Asp Thr Ala Phe Gly Gly Gly Thr Lys Val Glu Ile Lys Arg Thr
            100                 105                 110

<210> SEQ ID NO 93
<211> LENGTH: 112
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 93

Asp Ile Gln Met Thr Gln Ser Pro Ser Thr Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Phe Ala Ser Lys Leu Ala Ser Gly Val Pro Ser Arg Phe Lys Gly
50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Gln Thr Val Ser Tyr Lys Asn
                85                  90                  95

Ala Asp Thr Ala Phe Gly Gly Gly Thr Lys Val Glu Ile Lys Arg Thr
            100                 105                 110

<210> SEQ ID NO 94
<211> LENGTH: 119
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 94

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Val
            20                  25                  30

Ser Ile Ser Trp Ile Arg Gln Pro Pro Gly Lys Gly Leu Glu Trp Ile
        35                  40                  45

Gly Thr Ile Gly Ala Ser Gly Ser Ala Tyr Tyr Ala Ser Trp Ala Lys
50                  55                  60

Arg Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Glu Ile Leu Tyr Tyr Gly Met Asp Leu Trp Gly Gln Gly Thr Leu
            100                 105                 110

Val Thr Val Ser Ser Ala Ser
        115

<210> SEQ ID NO 95
<211> LENGTH: 119
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 95

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ser Val
            20                  25                  30

Ser Ile Ser Trp Ile Arg Gln Pro Pro Gly Lys Gly Leu Glu Trp Ile
        35                  40                  45

Gly Thr Ile Gly Ala Ser Gly Ser Ala Tyr Tyr Ala Ser Trp Ala Lys
            50                  55                  60

Arg Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                        85                  90                  95

Lys Glu Ile Leu Tyr Tyr Gly Met Asp Leu Trp Gly Gln Gly Thr Leu
                100                 105                 110

Val Thr Val Ser Ser Ala Ser
            115

<210> SEQ ID NO 96
<211> LENGTH: 119
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ser Ile Ser Trp Val Arg Gln Ala Pro Gly Lys Gly Leu Glu Trp Val
        35                  40                  45

Ser Thr Ile Gly Ala Ser Gly Ser Ala Tyr Tyr Ala Ser Trp Ala Lys
    50                  55                  60

Arg Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Glu Ile Leu Tyr Tyr Gly Met Asp Leu Trp Gly Gln Gly Thr Leu
                100                 105                 110

Val Thr Val Ser Ser Ala Ser
            115

<210> SEQ ID NO 97
<211> LENGTH: 119
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Thr Val Ser Gly Ile Asp Leu Ser Ser Val
            20                  25                  30

Ser Ile Ser Trp Val Arg Gln Ala Pro Gly Lys Gly Leu Glu Trp Val
        35                  40                  45

Ser Thr Ile Gly Ala Ser Gly Ser Ala Tyr Tyr Ala Ser Trp Ala Lys
    50                  55                  60

Arg Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

```
Lys Glu Ile Leu Tyr Tyr Gly Met Asp Leu Trp Gly Gln Gly Thr Leu
            100                 105                 110

Val Thr Val Ser Ser Ala Ser
        115

<210> SEQ ID NO 98
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Glu Pro Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Gly Ser Thr Ser
                85                  90                  95

Ser Ser Asp Tyr Gly Asn Ala Phe Gly Gly Gly Thr Lys Val Glu Ile
            100                 105                 110

Lys Arg Thr
        115

<210> SEQ ID NO 99
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Glu Pro Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Gly Ser Thr Ser
                85                  90                  95

Ser Ser Asp Tyr Gly Asn Ala Phe Gly Gly Gly Thr Lys Val Glu Ile
            100                 105                 110

Lys Arg Thr
        115

<210> SEQ ID NO 100
<211> LENGTH: 115
```

<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Glu Pro Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Ser Thr Tyr Gly Ser Thr Ser
                85                  90                  95

Ser Ser Asp Tyr Gly Asn Ala Phe Gly Gly Gly Thr Lys Val Glu Ile
            100                 105                 110

Lys Arg Thr
        115

<210> SEQ ID NO 101
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Asn Leu Glu Pro Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Cys Thr Tyr Gly Ser Thr Ser
                85                  90                  95

Ser Ser Asp Tyr Gly Asn Ala Phe Gly Gly Gly Thr Lys Val Glu Ile
            100                 105                 110

Lys Arg Thr
        115

<210> SEQ ID NO 102
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 102

Asp Ile Gln Met Thr Gln Ser Pro Ser Ser Leu Ser Ala Ser Val Gly

Asp Arg Val Thr Ile Thr Cys Gln Ala Ser Gln Ser Ile Ser Asn Tyr
            20                  25                  30

Leu Ala Trp Tyr Gln Gln Lys Pro Gly Lys Arg Pro Lys Leu Leu Ile
            35                  40                  45

Tyr Ala Ala Ser Asn Leu Glu Pro Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Ser Tyr Gly Ser Thr Ser
            85                  90                  95

Ser Ser Asp Tyr Gly Asn Ala Phe Gly Gly Gly Thr Lys Val Glu Ile
            100                 105                 110

Lys Arg Thr
        115

<210> SEQ ID NO 103
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ala Trp Tyr Gln Gln Lys Pro Gly Lys Arg Pro Lys Leu Leu Ile
            35                  40                  45

Tyr Ala Ala Ser Asn Leu Glu Pro Gly Val Pro Ser Arg Phe Ser Gly
            50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Cys Thr Tyr Gly Ser Thr Ser
            85                  90                  95

Ser Ser Asp Tyr Gly Asn Ala Phe Gly Gly Gly Thr Lys Val Glu Ile
            100                 105                 110

Lys Arg Thr
        115

<210> SEQ ID NO 104
<211> LENGTH: 115
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Tyr
            20                  25                  30

Leu Ala Trp Tyr Gln Gln Lys Pro Gly Lys Arg Pro Lys Leu Leu Ile
            35                  40                  45

Tyr Ala Ala Ser Asn Leu Glu Pro Gly Val Pro Ser Arg Phe Ser Gly

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Gly Ser Thr Ser
                85                  90                  95

Ser Ser Asp Tyr Gly Asn Ala Phe Gly Gly Gly Thr Lys Val Glu Ile
            100                 105                 110

Lys Arg Thr
        115

<210> SEQ ID NO 105
<211> LENGTH: 1392
<212> TYPE: DNA
<213> ORGANISM: Oryctolagus cuniculus
<220> FEATURE:
<221> NAME/KEY: misc_feature
<223> OTHER INFORMATION: HC

<400> SEQUENCE: 105

```
atggaattgg ggctgagctg ggttttcctt gttgctattt tagaaggtgt ccagtgtgag      60
gtgcagctgt tggagtctgg gggaggcttg gtacagcctg gggggtccct gagactctcc     120
tgtacagtct ctggattcac cctcagtagc atttcgatag ctgggtccg ccaggctcca     180 ggaaggggc tggagtgggt ctcaaccatt agtgacagtg gtagcgcata ctacgcgagc     240
tgggcgaaaa gccggttcac catctccaga gacaattcca gaacacgct gtatctgcaa     300 atgaacagcc tgagagccga ggacacggcc gtatattact gtgcgaaaga aatcctttac     360
tacggcatgg acctctgggg ccagggcacc ctggtcaccg tctcctcagc tagcaccaag     420
ggcccatcgg tcttcccct ggcgccctgc tccaggagca cctccgagag cacagccgcc     480
ctgggctgcc tggtcaagga ctacttcccc gaaccggtga cggtgtcgtg aactcaggc     540 gccctgacca gcggcgtgca caccttcccg gctgtcctac agtcctcagg actctactcc     600
ctcagcagcg tggtgaccgt gccctccagc agcttgggca cgaagaccta cacctgcaac     660
gtagatcaca gcccagcaa caccaaggtg gacaagagag ttgagtccaa atatggtccc     720
ccatgcccac catgcccagc acctgagttc ctggggggac catcagtctt cctgttcccc     780
ccaaaaccca aggacactct catgatctcc cggacccctg aggtcacgtg cgtggtggtg     840
gacgtgagcc aggaagaccc cgaggtccag ttcaactggt acgtggatgg cgtggaggtg     900
cataatgcca agacaaagcc gcgggaggag cagttcaaca gcacgtaccg tgtggtcagc     960
gtcctcaccg tcctgcacca ggactggctg aacggcaagg agtacaagtg caaggtctcc    1020
aacaaaggcc tcccgtcctc catcgagaaa accatctcca aagccaaagg gcagccccga    1080
gagccacagg tgtacaccct gcccccatcc caggaggaga tgaccaagaa ccaggtcagc    1140
ctgacctgcc tggtcaaagg cttctacccc agcgacatcg ccgtggagtg ggagagcaat    1200
gggcagccgg agaacaacta caagaccacg cctcccgtgc tggactccga cggctccttc    1260
ttcctctaca gcaggctcac cgtggacaag agcaggtggc aggaggggaa tgtcttctca    1320
tgctccgtga tgcatgaggc tctgcacaac cactacacac agaagagcct ctccctgtct    1380
ccgggtaaat ga                                                        1392
```

<210> SEQ ID NO 106
<211> LENGTH: 729
<212> TYPE: DNA
<213> ORGANISM: Oryctolagus cuniculus
<220> FEATURE:

<221> NAME/KEY: misc_feature
<223> OTHER INFORMATION: LC

<400> SEQUENCE: 106

```
atggacatga gggtccccgc tcagctcctg gggctcctgc tactctggct ccgaggtgcc      60
agatgtgaca tccagatgac ccagtctcca tcctccctgt ctgcatctgt aggagacaga     120
gtcaccatca cttgccaggc cagtgaggac attgaaagct atttagcctg gtatcagcag     180
aaaccaggga aagcccctaa gctcctgatc tatgctgcat ccaatctgga gcctggggtc     240
ccatcaaggt tcagtggcag tggatctggg acagatttca ctctcaccat cagcagtctg     300
caacctgaag attttgcaac ttactactgt caagctactt atggtagtac tagtagtagt     360
gattatggta atgctttcgg cggagggacc aaggtggaaa tcaaacgtac ggtggctgca     420
ccatctgtct tcatcttccc gccatctgat gagcagttga aatctggaac tgcctctgtt     480
gtgtgcctgc tgaataactt ctatcccaga gaggccaaag tacagtggaa ggtggataac     540
gccctccaat cgggtaactc ccaggagagt gtcacagagc aggacagcaa ggacagcacc     600
tacagcctca gcagcaccct gacgctgagc aaagcagact acgagaaaca caaagtctac     660
gcctgcgaag tcacccatca gggcctgagt tcgcccgtca caaagagctt caacagggga     720
gagtgttag                                                             729
```

<210> SEQ ID NO 107
<211> LENGTH: 1401
<212> TYPE: DNA
<213> ORGANISM: Oryctolagus cuniculus
<220> FEATURE:
<221> NAME/KEY: misc_feature
<223> OTHER INFORMATION: HC

<400> SEQUENCE: 107

```
atggaacttg gactgtcttg ggtgtttctt gtcgctatcc tggaaggagt gcaatgcgaa      60
gtgcagctgg tcgaaagcgg aggcggactg gtccaacctg gcggatccct gagactgtcc     120
tgtgccgcct ccggttttac cctgagcagc aacgccatgt cctgggtcag acaggcacca     180
ggaaaagggc tggagtggat cggttgcatt gtgtacggga attgctacta cgccagctgg     240
gtgaacggac ggttcaccat cagctcagat aattcaaaga caccccttta cctccaaatg     300
aactccctgc gcgcagagga tactgccgtg tactactgcg ccaggatccc tgccggatcg     360
tcggtctaca ccgggggctt caacatctgg ggtcaaggca ccctcgtgac cgtgagctct     420
gcgtcgacca agggcccgtc cgtgttcccg ctggccccat gctcacgctc gacctccgag     480
tccacagccg cactgggctg cttggtcaaa gactacttcc ctgaacccgt cactgtgtcg     540
tggaacagcg ggctctcaca cagcggcgtg cataccttc cggcggtgct tcagagctcc      600
ggactgtact ccctctcgtc cgtcgtgact gtcccctcct cgtccctggg caccaagacc     660
tacacttgca atgtggacca caagcccctcg aacaccaaag tggacaagcg ggtggagtcg    720
aagtatggtc cgccatgccc tccttgtcct gcgcccgagt ttctgggagg ccatccgtg     780
ttcctcttcc cgccgaagcc gaaggacacc ctgatgattt cccgcactcc tgaagtgacc     840
tgtgtggtgg tggacgtgtc ccaggaagat ccggaagtgc agttcaattg gtatgtggac     900
ggagtcgagg tgcacaacgc aaagactaag cctagggagg aacagttcaa ctccacctac     960
cgcgtggtgt cagtgctgac ggtgctgcac caggactggt tgaacggcaa agagtacaag    1020
tgcaaggtgt ccaacaaggg actgccgtcc agcatcgaaa agaccatctc caaggccaag    1080
ggacagccca gagaaccgca agtgtacacc ctcccgccaa gccaggaaga gatgaccaag    1140
```

```
aaccaagtgt ccctgacttg cctcgtgaag ggattctacc cctccgacat cgccgtggaa    1200
tgggaatcaa atggacagcc cgaaaacaac tacaagacca cgccgcctgt gctggactcg    1260
gacggttcct tcttcctgta ctcccgcctc accgtcgata agtcacggtg caggaggggg    1320
aacgtgttca gctgctccgt catgcacgaa gcgctccaca accattatac tcagaagtcc    1380
ctgtccttgt cccccggaaa g                                              1401
```

<210> SEQ ID NO 108
<211> LENGTH: 717
<212> TYPE: DNA
<213> ORGANISM: Oryctolagus cuniculus
<220> FEATURE:
<221> NAME/KEY: misc_feature
<223> OTHER INFORMATION: LC

<400> SEQUENCE: 108

```
atggatatga gagtgcctgc ccaactcctc ggacttctgc tgctttggtt gagaggtgcc     60
agatgcgata tccaaatgac ccagtcaccg tccaccctga cgcctctgt gggcgaccgc    120 gtcactatca cttgccaagc ctcggagaac atctattcct tcctggcctg gtaccagcag    180
aaaccgggga aggctcctaa gctgctcatc tacttcgcgt ccaagctggc ctccggagtg    240
ccatcacggt tctctggaag cgggagcgga acccagttca ccctgactat tagctccttg    300
caacccgacg acttcgcgac ctactactgt cagcagaccc tgtcctacaa gaacgcggat    360
acagcctttg gtggcgggac taaggtcgaa attaagcgta cggtggctgc tccatccgtg    420
ttcatcttcc cgccttccga cgagcagctg aagtccggta ccgcaagcgt ggtctgcctg    480
ctcaacaact ctaccccccg cgaagccaag gtccagtgga aggtggacaa cgcactccag    540
tcggggaatt cacaggaaag cgtgactgag caagattcca aggactcgac ctactcgctg    600
tcctccaccc tgactctgtc caaggccgac tacgaaaagc acaaggtcta tgcctgtgaa    660
gtgacccacc agggactttc cagccccgtg acgaaatcct tcaaccgggg agagtgc      717
```

<210> SEQ ID NO 109
<211> LENGTH: 1404
<212> TYPE: DNA
<213> ORGANISM: Oryctolagus cuniculus
<220> FEATURE:
<221> NAME/KEY: misc_feature
<223> OTHER INFORMATION: HC

<400> SEQUENCE: 109

```
atggagttct ggttgtcctg ggtgttcctc gtcgctattc ttaagggagt gcagtgtgaa     60
gtgcagcttg tcgagtccgg cggcggactc gtgcagcccg gcggaagcct gagactctcc    120
tgcgccgcct cggattcga cctctcatcc aacgccatgt gctgggtccg acaggccccg    180
gggaagggtc tggagtggat cggttgcatt gtgtacggaa acttctacta cgcgtcctgg    240
gtcaagggcc ggttcaccat ttccaccgat aacgccaaga ctccctcta cctccaaatg    300 aacagcctga gggctgagga cactgcggtg tacttttgcg cccgggatcc cgccgggtcc    360
tccgtgtaca ctggagggtt caacatctgg ggccagggta ccctcgtgac tgtcagcagc    420
gctagcacta aggggccctc cgtgttcccc ctggcgcctt gttcccgctc cacctctgaa    480
tccaccgctg ccctgggctg cctcgtgaag gactacttcc ctgaaccggt cactgtgtcc    540
tggaactccg gagccttgac ttcgggtgtc cacacttttc ccgccgtgct gcaatcaagc    600
ggtctgtact ccctgagctc ggtcgtgact gtgcccagct cgtcgctcgg aaccaagacc    660
```

```
tacacgtgca acgtcgacca caagccgtcg aacacgaagg tcgataagcg cgtggagtcc    720
aaatacggac cccttgtcc gccatgccca gccccgaat tcctgggcgg ccccagcgtg     780
ttcctgttcc cgcctaaacc gaaggacact ctgatgatca gccggacccc ggaagtgaca    840
tgcgtggtgg tggacgtgtc ccaggaagat ccagaagtcc agttcaattg gtacgtcgac    900
ggcgtggaag tgcacaacgc aaagaccaag ccccgcgagg aacagttcaa ttccacctac    960
cgcgtggtgt ccgtgctgac cgtgctgcat caggactggc tgaacggaaa ggagtacaaa   1020
tgcaaagtgt ccaacaaggg actgccttca agcattgaaa agaccatctc caaggccaag   1080
gggcagccta gagagccaca agtgtacacc ctgccccctt cacaagagga atgaccaag    1140 aaccaagtgt cgctgacctg tctggtcaag ggattctacc cgagcgatat cgcagtggaa   1200
tgggagagca atggccagcc tgagaacaac tacaagacca cccgccggt gctcgactcc    1260 gacggttcat ttttcttgta ttcccggctg actgtggaca agtcacggtg gcaggagggc   1320
aacgtgttct cctgctccgt gatgcatgaa gccctgcaca accactatac ccagaagtcg   1380
ctgtccctgt cgttggggaa gtga                                          1404
```

<210> SEQ ID NO 110
<211> LENGTH: 720
<212> TYPE: DNA
<213> ORGANISM: Oryctolagus cuniculus
<220> FEATURE:
<221> NAME/KEY: misc_feature
<223> OTHER INFORMATION: LC

<400> SEQUENCE: 110

```
atggatatgc gcgtgcttgc ccaactgctc ggactccttc tgctctgctt tcccggtgct     60
agatgcgaca tccagatgac tcagagccct tcctccctgt ccgcctccgt gggcgatagg    120
gtcacaatta cttgtcaagc ctccgaaaac atctatagct tcctcgcgtg gtaccagcag    180
aagccaggaa agagcccaa gccgctgatc tatttcgcgt ctaagttggc ctccggagtg    240
ccgtcccggt tctcgggatc aggttcaggg actgacttca ctctgaccat tagctcgctg    300
caacccgaag atttcgccac ctactactgc cagcaaaacg tgtcctacaa gaacgccgac    360
actgcgttcg gccagggcac caaagtggag atcaagcgta cggtggccgc ccgtccgtg    420 ttcatctttc cgccttccga cgaacagctg aagtcgggaa ccgcatccgt cgtgtgcctg    480
ctgaacaact ctacccacg cgaagctaaa gtgcagtgga agtggataa tgcactgcag    540 tccggaaact cgcaggagag cgtgaccgag caggactcaa aggactccac ttactccctg    600
tcgtccaccc tgacgttgag caaggccgac tacgagaagc acaaggtcta cgcctgcgaa    660
gtgacccatc agggcctgag ctcgcccgtc accaagtcat tcaaccgggg ggagtgttga   720
```

<210> SEQ ID NO 111
<211> LENGTH: 123
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Ser Ser Asn
            20                  25                  30

Ala Met Cys Trp Val Arg Gln Ala Pro Gly Lys Gly Leu Glu Trp Ile

```
                35                  40                  45
Gly Cys Ile Val Tyr Gly Asn Cys Tyr Tyr Ala Ser Trp Val Lys Gly
        50                  55                  60
Arg Phe Thr Ile Ser Thr Asp Asn Ala Lys Asn Ser Leu Tyr Leu Gln
65                  70                  75                  80
Met Asn Ser Leu Arg Ala Glu Asp Thr Ala Val Tyr Phe Cys Ala Arg
                85                  90                  95
Asp Pro Ala Gly Ser Ser Val Tyr Thr Gly Gly Phe Asn Ile Trp Gly
            100                 105                 110
Gln Gly Thr Leu Val Thr Val Ser Ser Ala Ser
        115                 120

<210> SEQ ID NO 112
<211> LENGTH: 123
<212> TYPE: PRT
<213> ORGANISM: Oryctolagus cuniculus
<220> FEATURE:
<221> NAME/KEY: MISC_FEATURE
<223> OTHER INFORMATION: VH

<400> SEQUENCE: 112

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asp Leu Ser Ser Asn
            20                  25                  30
Ala Met Cys Trp Val Arg Gln Ala Pro Gly Lys Gly Leu Glu Trp Ile
        35                  40                  45
Gly Cys Ile Val Tyr Gly Asn Phe Tyr Tyr Ala Ser Trp Val Lys Gly
        50                  55                  60
Arg Phe Thr Ile Ser Thr Asp Asn Ala Lys Asn Ser Leu Tyr Leu Gln
65                  70                  75                  80
Met Asn Ser Leu Arg Ala Glu Asp Thr Ala Val Tyr Phe Cys Ala Arg
                85                  90                  95
Asp Pro Ala Gly Ser Ser Val Tyr Thr Gly Gly Phe Asn Ile Trp Gly
            100                 105                 110
Gln Gly Thr Leu Val Thr Val Ser Ser Ala Ser
        115                 120

<210> SEQ ID NO 113
<211> LENGTH: 112
<212> TYPE: PRT
<213> ORGANISM: Oryctolagus cuniculus
<220> FEATURE:
<221> NAME/KEY: MISC_FEATURE
<223> OTHER INFORMATION: VK

<400> SEQUENCE: 113

Asp Ile Gln Met Thr Gln Ser Pro Ser Ser Leu Ser Ala Ser Val Gly
1               5                   10                  15
Asp Arg Val Thr Ile Thr Cys Gln Ala Ser Glu Asn Ile Tyr Ser Phe
            20                  25                  30
Leu Ala Trp Tyr Gln Gln Lys Pro Gly Lys Ser Pro Lys Pro Leu Ile
        35                  40                  45
Tyr Phe Ala Ser Lys Leu Ala Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Thr Val Ser Tyr Lys Asn
```

```
                85                  90                  95
Ala Asp Thr Ala Phe Gly Gln Gly Thr Lys Val Glu Ile Lys Arg Thr
            100                 105                 110

<210> SEQ ID NO 114
<211> LENGTH: 448
<212> TYPE: PRT
<213> ORGANISM: Oryctolagus cuniculus
<220> FEATURE:
<221> NAME/KEY: MISC_FEATURE
<223> OTHER INFORMATION: HC

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Leu Ser Ser Asn
            20                  25                  30

Ala Met Cys Trp Val Arg Gln Ala Pro Gly Lys Gly Leu Glu Trp Ile
        35                  40                  45

Gly Cys Ile Val Tyr Gly Asn Phe Tyr Tyr Ala Ser Trp Val Lys Gly
    50                  55                  60

Arg Phe Thr Ile Ser Thr Asp Asn Ala Lys Asn Ser Leu Tyr Leu Gln
65                  70                  75                  80

Met Asn Ser Leu Arg Ala Glu Asp Thr Ala Val Tyr Phe Cys Ala Arg
                85                  90                  95

Asp Pro Ala Gly Ser Ser Val Tyr Thr Gly Gly Phe Asn Ile Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335
```

```
Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 115
<211> LENGTH: 217
<212> TYPE: PRT
<213> ORGANISM: Oryctolagus cuniculus
<220> FEATURE:
<221> NAME/KEY: MISC_FEATURE
<223> OTHER INFORMATION: LC

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ser Pro Lys Pro Leu Ile
            35                  40                  45

Tyr Phe Ala Ser Lys Leu Ala Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Ser Tyr Lys Asn
                85                  90                  95

Ala Asp Thr Ala Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
            210                 215
```

PD-L1 SPECIFIC MONOCLONAL ANTIBODIES FOR DISEASE TREATMENT AND DIAGNOSIS

Human cancers harbor numerous genetic and epigenetic alterations, generating neoantigens potentially recognizable by the immune system (Sjoblom et al., *Science* 314:268-74 (2006)). Although an endogenous immune response to cancer is observed in preclinical models and patients, this response is ineffective, and established cancers are viewed as "self" and tolerated by the immune system. Contributing to this state of tolerance, tumors may exploit several distinct mechanisms to actively suppress the host immune response (Topalian et al., *J Clin Oncol* 29:4828-36 (2011); Mellman et al., *Nature* 480:480-489 (2011)). Among these mechanisms, endogenous "immune checkpoints" that normally terminate immune responses to mitigate collateral tissue damage can be co-opted by tumors to evade immune destruction. Efforts to develop specific immune checkpoint pathway inhibitors have begun to provide new immunotherapeutic approaches for treating cancer, including the development of the anti-CTLA-4 antibody, ipilimumab, for the treatment of patients with advanced melanoma (Nodi et al., *New Engl J Med* 363:711-23 (2010)).

Programmed Death-1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1 (Freeman et al., *J. Exp. Med.* 192(7): 1027-34 (2000); Latchm an et al., *Nat Immunol* 2:261-8 (2001)).

PD-1 primarily functions in peripheral tissues where activated T-cells may encounter the immunosuppressive PD-L1 (also called B7-H1 or CD274) and PD-L2 (B7-DC) ligands expressed by tumor and/or stromal cells (Flies et al., *Yale J Biol Med* 84:409-21 (2011); Topalian et al., *Curr Opin Immuno* 24:1-6 (2012)).

Inhibition of the PD-1/PD-L1 interaction mediates potent antitumor activity in preclinical models (U.S. Pat. Nos. 8,008,449 and 7,943,743). It appears that upregulation of PD-L1 may allow cancers to evade the host immune system. An analysis of 196 tumor specimens from patients with renal cell carcinoma found that high tumor expression of PD-L1 was associated with increased tumor aggressiveness and a 4.5-fold increased risk of death (Thompson et al., *Proc Natl Acad Sci USA* 101 (49): 17174-9 (2004)). Ovarian cancer patients with higher expression of PD-L1 had a significantly poorer prognosis than those with lower expression. PD-L1 expression correlated inversely with intraepithelial CD8+ T-lymphocyte count, suggesting that PD-L1 on tumor cells may suppress antitumor CD8+ T cells (Hamanishi et al., *Proc Natl Acad Sci USA* 104 (9): 3360-3365 (2007)).

PD-L1 has also been implicated in infectious disease, in particular chronic infectious disease. Cytotoxic CD8 T lymphocytes (CTLs) play a pivotal role in the control of infection. Activated CTLs, however, often lose effector function during chronic infection. PD-1 receptor and its ligand PD-L1 of the B7/CD28 family function as a T cell co-inhibitory pathway and are emerging as major regulators converting effector CTLs into exhausted CTLs during chronic infection with human immunodeficiency virus, hepatitis B virus, hepatitis C virus, herpes virus, and other bacterial, protozoan, and viral pathogens capable of establishing chronic infections. Such bacterial and protozoal pathogens can include *E. coli*, *Staphylococcus* sp., *Streptococcus* sp., *Mycobacterium tuberculosis*, *Giardia*, *Malaria*, *Leishmania*, and *Pseudomonas aeruginosa*. Importantly, blockade of the PD-1/PD-L1 pathway is able to restore functional capabilities to exhausted CTLs. PD1/PD-L1 is thus a target for developing effective prophylactic and therapeutic vaccination against chronic bacterial and viral infections (see, e.g., Hofmeyer et al., *Journal of Biomedicine and Biotechnology*, vol. 2011, Article ID 451694, 9 pages, doi:10.1155/2011/451694).

Recent studies have also shown that systemic immune suppression may curtail the ability to mount the protective, cell-mediated immune responses that are needed for brain repair in neurodegenerative diseases. By using mouse models of Alzheimer's disease, immune checkpoint blockade directed against the programmed death-1 (PD-1) pathway was shown to evoke an interferon γ-dependent systemic immune response, which was followed by the recruitment of monocyte-derived macrophages to the brain. When induced in mice with established pathology, this immunological response led to clearance of cerebral amyloid-β (Aβ) plaques and improved cognitive performance. These findings suggest that immune checkpoints may be targeted therapeutically in neurodegenerative disease such as Alzheimer's disease using antibodies to PD-L1 (see, e.g., Baruch et al., *Nature Medicine*, January 2016, doi:10.1038/nm.4022).

Specific antibodies to PD-L1 have been developed as anti-cancer agents (see U.S. Pat. Nos. 9,212,224 and 8,008,449). The use of Ab inhibitors of the PD-1/PD-L1 interaction for treating cancer has entered clinical trials (Brahmer et al., *J Clin Oncol* 28:3167-75 (2010); Flies et al., *Yale J Biol Med* 84:409-21 (2011); Topalian et al., *N Engl J Med* 366:2443-54 (2012); Brahmer et al., *N Engl J Med* 366: 2455-65 (2012)). There exists a need however, for anti-PD-L1 antibodies useful in the treatment of cancer, infectious disease, and neurodegenerative disease, e.g., Alzheimer's disease. The present application fulfills this and other needs.

SUMMARY

In one aspect, the present invention provides an antibody which binds to human PD-L1 protein, the antibody selected from the group consisting of:

(1) an antibody comprising a heavy chain variable region comprising heavy chain CDR1 having the amino acid sequence as set forth in SEQ ID NO: 19, heavy chain CDR2 having the amino acid sequence as set forth in SEQ ID NO: 20, and heavy chain CDR3 having the amino acid sequence as set forth in SEQ ID NO: 21, and a light chain variable region comprising light chain CDR1 having the amino acid sequence as set forth in SEQ ID NO: 22, light chain CDR2 having the amino acid sequence as set forth in SEQ ID NO: 23, and light chain CDR3 having the amino acid sequence as set forth in SEQ ID NO: 24;

(2) an antibody comprising a heavy chain variable region comprising heavy chain CDR1 having the amino acid sequence as set forth in SEQ ID NO: 25, heavy chain CDR2 having the amino acid sequence as set forth in SEQ ID NO: 26, and heavy chain CDR3 having the amino acid sequence as set forth in SEQ ID NO: 27, and a light chain variable region comprising light chain CDR1 having the amino acid sequence as set forth in SEQ ID NO: 28, light chain CDR2 having the amino acid sequence as set forth in SEQ ID NO:

29, and light chain CDR3 having the amino acid sequence as set forth in SEQ ID NO: 30;

(3) an antibody comprising a heavy chain variable region comprising heavy chain CDR1 having the amino acid sequence as set forth in SEQ ID NO: 31, heavy chain CDR2 having the amino acid sequence as set forth in SEQ ID NO: 32, and heavy chain CDR3 having the amino acid sequence as set forth in SEQ ID NO: 33, and a light chain variable region comprising light chain CDR1 having the amino acid sequence as set forth in SEQ ID NO: 34, light chain CDR2 having the amino acid sequence as set forth in SEQ ID NO: 35, and light chain CDR3 having the amino acid sequence as set forth in SEQ ID NO: 36;

(4) an antibody comprising a heavy chain variable region comprising heavy chain CDR1 having the amino acid sequence as set forth in SEQ ID NO: 37, heavy chain CDR2 having the amino acid sequence as set forth in SEQ ID NO: 38, and heavy chain CDR3 having the amino acid sequence as set forth in SEQ ID NO: 39, and a light chain variable region comprising light chain CDR1 having the amino acid sequence as set forth in SEQ ID NO: 40, light chain CDR2 having the amino acid sequence as set forth in SEQ ID NO: 41, and light chain CDR3 having the amino acid sequence as set forth in SEQ ID NO: 42;

(5) an antibody comprising a heavy chain variable region comprising heavy chain CDR1 having the amino acid sequence as set forth in SEQ ID NO: 43, heavy chain CDR2 having the amino acid sequence as set forth in SEQ ID NO: 44, and heavy chain CDR3 having the amino acid sequence as set forth in SEQ ID NO: 45, and a light chain variable region comprising light chain CDR1 having the amino acid sequence as set forth in SEQ ID NO: 46, light chain CDR2 having the amino acid sequence as set forth in SEQ ID NO: 47, and light chain CDR3 having the amino acid sequence as set forth in SEQ ID NO: 48;

(6) an antibody comprising a heavy chain variable region comprising heavy chain CDR1 having the amino acid sequence as set forth in SEQ ID NO: 49, heavy chain CDR2 having the amino acid sequence as set forth in SEQ ID NO: 50, and heavy chain CDR3 having the amino acid sequence as set forth in SEQ ID NO: 51, and a light chain variable region comprising light chain CDR1 having the amino acid sequence as set forth in SEQ ID NO: 52, light chain CDR2 having the amino acid sequence as set forth in SEQ ID NO: 53, and light chain CDR3 having the amino acid sequence as set forth in SEQ ID NO: 54;

(7) an antibody comprising a heavy chain variable region comprising heavy chain CDR1 having the amino acid sequence as set forth in SEQ ID NO: 55, heavy chain CDR2 having the amino acid sequence as set forth in SEQ ID NO: 56, and heavy chain CDR3 having the amino acid sequence as set forth in SEQ ID NO: 57, and a light chain variable region comprising light chain CDR1 having the amino acid sequence as set forth in SEQ ID NO: 58, light chain CDR2 having the amino acid sequence as set forth in SEQ ID NO: 59, and light chain CDR3 having the amino acid sequence as set forth in SEQ ID NO: 60;

(8) an antibody comprising a heavy chain variable region comprising heavy chain CDR1 having the amino acid sequence as set forth in SEQ ID NO: 61, heavy chain CDR2 having the amino acid sequence as set forth in SEQ ID NO: 62, and heavy chain CDR3 having the amino acid sequence as set forth in SEQ ID NO: 63, and a light chain variable region comprising light chain CDR1 having the amino acid sequence as set forth in SEQ ID NO: 64, light chain CDR2 having the amino acid sequence as set forth in SEQ ID NO: 65, and light chain CDR3 having the amino acid sequence as set forth in SEQ ID NO: 66; and (9) an antibody comprising a heavy chain variable region comprising heavy chain CDR1 having the amino acid sequence as set forth in SEQ ID NO: 67, heavy chain CDR2 having the amino acid sequence as set forth in SEQ ID NO: 68, and heavy chain CDR3 having the amino acid sequence as set forth in SEQ ID NO: 69, and a light chain variable region comprising light chain CDR1 having the amino acid sequence as set forth in SEQ ID NO: 70, light chain CDR2 having the amino acid sequence as set forth in SEQ ID NO: 71, and light chain CDR3 having the amino acid sequence as set forth in SEQ ID NO: 72.

In one aspect, the present invention provides an antibody which binds to human PD-L1 protein, comprising a heavy chain variable domain selected from the group consisting of SEQ ID NO: 1, 2, 3, 4, 5, 6, 7, 8, and 9, and in another aspect the present invention provides an antibody which binds to human PD-L1 protein comprising a light chain variable domain selected from the group consisting of SEQ ID NO: 10, 11, 12, 13, 14, 15, 16, 17 and 18.

In one embodiment, the antibody is humanized. In another embodiment, the CDR domains of the antibody have one, two, three, four or five amino acids mutated, deleted or added.

In another aspect, the present invention provides a humanized antibody which binds to human PD-L1 protein comprising a heavy chain variable domain selected from the group consisting of SEQ ID NO: 73, 74, 75, 76, 77, 80, 81, 82, 83, 84, 86, 87, 88, 89, 94, 95, 96, 97, 111, and 112.

In another aspect, the present invention provides a humanized antibody which binds to human PD-L1 protein comprising a light chain variable domain selected from the group consisting of SEQ ID NO: 78, 79, 85, 90, 91, 92, 93, 98, 99, 100, 101, 102, 103, 104, and 113.

In another aspect, the present invention provides a humanized antibody which binds to human PD-L1 protein comprising a heavy chain variable domain having at least 95%, at least 96%, at least 97%, at least 98%, at least 99%, or at least 100% sequence identity to SEQ ID NO: 73, 74, 75, 76, 77, 80, 81, 82, 83, 84, 86, 87, 88, 89, 94, 95, 96, 97, 111 and 112.

In another aspect, the present invention provides a humanized antibody which binds to human PD-L1 protein comprising a light chain variable domain having at least 95%, at least 96%, at least 97%, at least 98%, at least 99%, or at least 100% sequence identity to SEQ ID NO: 78, 79, 85, 90, 91, 92, 93, 98, 99, 100, 101, 102, 103, 104, and 113.

In another aspect, the present invention provides a humanized antibody which binds to human PD-L1 protein comprising a heavy chain variable domain having at least 98%, at least 99%, or at least 100% sequence identity to SEQ ID NO: 114, and a light chain variable domain having at least 98%, at least 99%, or at least 100% sequence identity to SEQ ID NO: 115.

In one embodiment, the humanized antibody is a bispecific PD-L1antibody, which further comprises one or more binding domains, which bind to human TGF-Beta, TIGIT, LAG3, TIM3, CD39, or CD73.

In another aspect, the present invention provides a humanized antibody which binds to human PD-L1 protein comprising a heavy chain domain having at least 95%, at least 96%, at least 97%, at least 98%, at least 99%, or at least 100% sequence identity to SEQ ID NO: 105 and a light chain domain having at least 95%, at least 96%, at least 97%, at least 98%, at least 99%, or at least 100% sequence identity to SEQ ID NO: 106.

In another aspect, the present invention provides a humanized antibody which binds to human PD-L1 protein comprising a heavy chain domain having at least 95%, at least 96%, at least 97%, at least 98%, at least 99%, or at least 100% sequence identity to SEQ ID NO: 107 and a light chain domain having at least 95%, at least 96%, at least 97%, at least 98%, at least 99%, or at least 100% sequence identity to SEQ ID NO: 108.

In one aspect, the present invention provides a nucleic acid sequence which encodes a humanized human PD-L1 antibody heavy chain, having at least 95%, at least 96%, at least 97%, at least 98%, at least 99%, or at least 100% sequence identity to SEQ ID NO: 105; or having at least 95%, at least 96%, at least 97%, at least 98%, at least 99%, or at least 100% sequence identity to SEQ ID NO: 107; or having at least 95%, at least 96%, at least 97%, at least 98%, at least 99%, or at least 100% sequence identity to SEQ ID NO: 109.

In another aspect, the present invention provides a nucleic acid sequence which encodes a humanized human PD-L1 antibody light chain, having at least 95%, at least 96%, at least 97%, at least 98%, at least 99%, or at least 100% sequence identity to SEQ ID NO: 106; or having at least 95%, at least 96%, at least 97%, at least 98%, at least 99%, or at least 100% sequence identity to SEQ ID NO: 108; or having at least 95%, at least 96%, at least 97%, at least 98%, at least 99%, or at least 100% sequence identity to SEQ ID NO: 110.

In another aspect, the present invention provides a pharmaceutical composition comprising an antibody as described above.

In another aspect, the present invention provides a method of treating cancer, the method comprising the step of administering a pharmaceutical composition as described above to a subject in need thereof, wherein the cancer is selected from the group consisting of kidney, breast, lung, kidney, bladder, urinary tract, urethra, penis, vulva, vagina, cervical, colon, ovarian, prostate, pancreas, stomach, brain, head and neck, skin, uterine, testicular, esophagus, and liver cancer.

In another aspect, the present invention provides a method of treating an infectious disease, the method comprising the step of administering a pharmaceutical composition as described above to a subject in need thereof, wherein the infectious disease is a bacterial or viral disease.

In one embodiment, the infectious disease is a chronic infectious disease. In another embodiment, the viral disease is selected from the group consisting of hepatitis B virus (HBV), hepatitis C virus (HCV) or human immunodeficiency virus (HIV).

In another aspect, the present invention provides a method of treating a neurodegenerative disease, the method comprising the step of administering a pharmaceutical composition as described above to a subject in need thereof.

In one embodiment, the neurodegenerative disease is Alzheimer's disease.

BRIEF DESCRIPTION OF THE DRAWINGS

FIG. 1A-B. Example of PD-L1 binding assays on one 96-well B cell cloning plate showing clones cross-reactive with murine PD-L1.

FIG. 2A-C. Example of antigen binding ELISA for determination of mAb specificity. Rabbit IgG heavy and light chain v-regions were expressed as chimeric antibodies in HEK293 cells. Antibody containing supernatants were assayed by different ELISA.

FIG. 3A-B: Example of binding ELISA data for determination of anti-PD-L1 mAb cross-reactivity with monkey PD-L1 and human PDL2 using chimeric anti-PD-L1 antibodies. No cross reactivity to PDL2 was seen with any of the tested antibodies.

FIG. 4. Example of competition ELISA showing chimeric and humanized variants inhibit binding of PD1 to PD-L1.

FIG. 5. Example of SEB functional assay for evaluation of anti-PD-L1 mAb activity. Enhancement of SEB induced IL-2 secretion from whole blood by anti-PD-L1 mAbs compared to a commercially available mouse antibody (Biolegend, cat. #329710).

DETAILED DESCRIPTION OF THE INVENTION

Figure 6:
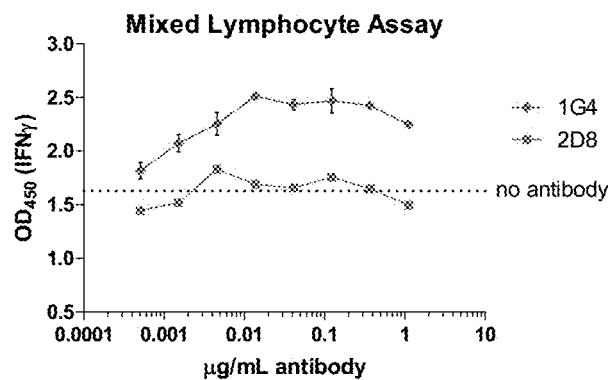
FIG. 6. Example of MLC functional assay for evaluation of anti-PD-L1 mAb activity. Although both mAbs bind PD-L1 only one (1G4) neutralizes PD-L1 signaling and enhances Interferon secretion.

The present invention relates to compositions and methods for immunotherapy of a subject afflicted with diseases such as cancer, an infectious disease, or a neurodegenerative disease, e.g., Alzheimer's disease, which methods comprise administering to the subject a composition comprising a therapeutically effective amount of an anti-PD-L1 antibody or portion thereof that potentiates an endogenous immune response, either stimulating the activation of the endogenous response or inhibiting the suppression of the endogenous response. In one embodiment, antibody is designated 111F1, 110E34, 115E2, 116F3, 113F1, 113G3, 115C1, 111H2 or 110H8, having the respective CDRs listed in Tables 4-12 below. In another embodiment, antibodies 111F1, 110E34, 115E2, 116F3, 113F1, 113G3, 115C1, 111H2 or 110H8 have the respective light and heavy chain variable regions as listed in Tables 2 and 3 below. In another embodiment, humanized antibodies 116F3, 113G3, 111H2 and 110H8 have respective heavy and light chain variable regions as shown in Tables 13-16 below. In another embodiment, humanized antibody 116F3 has the heavy and light chain as shown in Table 17, and humanized antibody 111H2 has the heavy and light chain as show in Table 17.

In certain other embodiments, the subject is selected as suitable for immunotherapy in a method comprising measuring the surface expression of PD-L1 in a test tissue sample obtained from a patient with cancer, infection, or a neurodegenerative disease of the tissue, for example, determining the proportion of cells in the test tissue sample that express PD-L1 on the cell surface, and selecting the patient for immunotherapy based on an assessment that PD-L1 is expressed on the surface of cells in the test tissue sample.

The "Programmed Death-1 (PD-1)" receptor refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under Genebank Accession No. U64863.

"Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under Genebank Accession No. Q9NZQ7.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing, isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The present composition encompasses amino acid substitutions in proteins and peptides, which do not generally alter the activity of the proteins or peptides (H. Neurath, R. L. Hill, *The Proteins*, Academic Press, New York, 1979). In one embodiment, these substitutions are "conservative" amino acid substitutions. The most commonly occurring substitutions are Ala/Ser, Val/Ile, Asp/Glu, Thr/Ser, Ala/Gly, Ala/Thr, Ser/Asn, Ala/Val, Ser/Gly, Ala/Pro, Lys/Arg, Asp/Asn, Leu/Ile, Leu/Val, Ala/Glu and Asp/Gly, in both directions As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Analogue as used herein denotes a peptide, polypeptide, or protein sequence which differs from a reference peptide, polypeptide, or protein sequence. Such differences may be the addition, deletion, or substitution of amino acids, phosphorylation, sulfation, acrylation, glycosylation, methylation, farnesylation, acetylation, amidation, and the like, the use of non-natural amino acid structures, or other such modifications as known in the art.

The term "unnatural amino acids" as used herein refers to amino acids other than the 20 typical amino acids found in the proteins in our human body. Unnatural amino acids are non-proteinogenic amino acids that either occur naturally or are chemically synthesized. They may include but are not limited to am inoisobutyric acid (Aib), β-amino acids ($β^3$ and $β^2$), homo-amino acids, proline and pyruvic acid derivatives, 3-substituted alanine derivatives. Glycine derivatives, ring-substituted phenylalanine and tyrosine derivatives, Linear core amino acids, diamino acids, D-amino acids and N-methyl amino acids.

Further an N-terminal amino acid may be modified by coupling an imidazolic group to the N-terminal amino acid of a polypeptide. Such imidzolic groups can be 4-imidazopropionyl (des-amino-histidyl), 4-amidzoacetyl, 5-imidazo-α, a dimethyl-acetyl. Coupling the imidazolic group to the peptide or portions thereof may be accomplished by synthetic chemical means. Because many of the various organic groups contemplated herein contain a carboxylic acid the imidazolic group can be added by solid phase protein synthesis analogous to adding an amino acid to the N-terminus of a polypeptide. Alternatively, an activated ester of the imidazolic group can be added by standard chemical reaction methods. Notation for these imidazolic groups may be denoted by "CA-"appearing prior to the N-terminal of a peptide or protein. In one embodiment the imidazolic group is a 4-imidzoacetyl group.

The anti-PD-L1 antibody of the invention designated 111F1, 110B4, 115E2, 116F3, 113F1, 113G3, 115C1, 111H2 or 110H8 may comprise a heavy chain CDR and a light chain CDR, wherein the heavy chain CDR comprises a sequence having at least 85%, at least 90%, at least 95%, at least 96%, at least 97%, at least 98%, at least 99% or 100% sequence identity to the respective CDRs listed in Tables 4-12 below, and wherein the light chain CDR comprises a sequence having at least 85%, at least 90%, at least 95%, at least 96%, at least 97%, at least 98%, at least 99% or 100% sequence identity to the respective CDRs listed in Tables 4-12 below.

The anti-PD-L1 antibody of the invention designated 111F1, 110B4, 115E2, 116F3, 113F1, 113G3, 115C1, 111H2 or 110H8 may comprise a heavy chain variable region and a light chain variable region, wherein the heavy chain variable region comprises a sequence having at least 95%, at least 96%, at least 97%, at least 98%, at least 99% or 100% sequence identity to the respective heavy chain variable regions listed in Table 2 below, and wherein the light chain variable region comprises a sequence having at least 95%, at least 96%, at least 97%, at least 98%, at least 99% or 100% sequence identity to the respective light chain variable regions listed in Table 3 below.

Humanized anti-PD-L1 antibodies 116F3, 113G3, 111H2, and 110H8 may comprise a heavy chain variable region and a light chain variable region, wherein the heavy chain variable region comprises a sequence having at least 95%, at least 96%, at least 97%, at least 98%, at least 99% or 100% sequence identity to the respective heavy chain variable regions listed in Tables 13-16 below, and wherein the light chain variable region comprises a sequence having at least 95%, at least 96%, at least 97%, at least 98%, at least 99% or 100% sequence identity to the respective light chain variable regions listed in Tables 13-16 below.

Humanized anti-PD-L1 antibodies 116F3 and 111H2 may comprise a heavy chain domain and a light chain domain, wherein the heavy chain domain comprises a sequence having at least 95%, at least 96%, at least 97%, at least 98%, at least 99% or 100% sequence identity to the respective heavy chain variable regions listed in Table 17 below, and wherein the light chain domain comprises a sequence having at least 95%, at least 96%, at least 97%, at least 98%, at least 99% or 100% sequence identity to the respective light chain domain listed in Table 17 below.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to VH—CH1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology, Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

Accordingly, in either aspect of the invention, the term antibody also embraces minibodies, diabodies, triabodies and the like. Diabodies are small bivalent biospecific antibody fragments with high avidity and specificity. Their high signal to noise ratio is typically better due to a better specificity and fast blood clearance increasing their potential for diagnostic and therapeutic targeting of specific antigen (Sundaresan et al., J Nucl Med 44:1962-9 (2003). In addition, these antibodies are advantageous because they can be engineered if necessary as different types of antibody fragments ranging from a small single chain Fv to an intact IgG with varying isoforms (Wu & Senter, Nat. Biotechnol. 23:1137-1146 (2005)). In some embodiments, the antibody fragment is part of a diabody. In some embodiments, in either aspect, the invention provides high avidity antibodies for use according to the invention.

The CDR regions provided by the invention may be used to construct an anti-PD-L1 binding protein, including without limitation, an antibody, a scFv, a triabody, a diabody, a minibody, and the like. In a certain embodiment, an anti-PD-L1 protein of the invention will comprise at least one CDR region from Tables 4-12 listed below or a sequence having at least 85%, at least 90%, at least 95%, at least 96%, at least 97%, at least 98%, at least 99% or 100% sequence identity to the CDR regions listed in Tables 4-12. Anti-PD-L1 binding proteins may comprise, for example, a CDR-H1, a CDR-H2, a CDR-H3, a CDR-L1, a CDR-L2, a CDR-L3, or combinations thereof, from an antibody provided herein. In particular embodiments of the invention, an anti-PD-L1 binding protein may comprise all three CDR-H sequences of an antibody provided herein, all three CDR-L sequences of an antibody provided herein, or both. Anti-PD-L1 CDR sequences may be used on an antibody backbone, or fragment thereof, and likewise may include humanized antibodies, or antibodies containing humanized sequences. In some embodiments, the CDR regions may be defined using the Kabat definition, the Chothia definition, the AbM definition, the contact definition, or any other suitable CDR numbering system.

In some embodiments, the invention provides antibodies (e.g., diabodies, minibodies, triabodies) or fragments thereof having the CDRs of Tables 4-12 or a sequence having at least 85%, at least 90%, at least 95%, at least 96%, at least 97%, at least 98%, at least 99% or 100% sequence identity to the CDRs of Tables 4-12. In other embodiments, the diabodies possess the light and heavy chain of Tables 2 and 3 or a sequence having at least 95%, at least 96%, at least 97%, at least 98%, at least 99% or 100% sequence identity to the sequences of Tables 2 and 3.

Diabodies, first described by Hollinger et al., PNAS (USA) 90(14): 6444-6448 (1993), may be constructed using heavy and light chains disclosed herein, as well as by using individual CDR regions disclosed herein. Typically, diabody fragments comprise a heavy chain variable domain (VH) connected to a light chain variable domain (VL) by a linker which is too short to allow pairing between the two domains on the same chain. Accordingly, the VH and VL domains of one fragment are forced to pair with the complementary VH and VL domains of another fragment, thereby forming two antigen-binding sites. Triabodies can be similarly constructed with three antigen-binding sites. An Fv fragment contains a complete antigen-binding site which includes a VL domain and a VH domain held together by non-covalent interactions. Fv fragments embraced by the present invention also include constructs in which the VH and VL domains are crosslinked through glutaraldehyde, intermolecular disulfides, or other linkers. The variable domains of the heavy and light chains can be fused together to form a single chain variable fragment (scFv), which retains the original specificity of the parent immunoglobulin. Single chain Fv (scFv) dimers, first described by Gruber et al., *J. Immunol.* 152(12):5368-74 (1994), may be constructed using heavy and light chains disclosed herein, as well as by using individual CDR regions disclosed herein. Many techniques known in the art can be used to prepare the specific binding constructs of the present invention (see, U.S. Patent Application Publication No. 20070196274 and U.S. Patent Application Publication No. 20050163782, which are each herein incorporated by reference in their entireties for all purposes, particularly with respect to minibody and diabody design).

Bispecific antibodies can be generated by chemical cross-linking or by the hybrid hybridoma technology. Alternatively, bispecific antibody molecules can be produced by recombinant techniques. Dimerization can be promoted by reducing the length of the linker joining the VH and the VL domain from about 15 amino acids, routinely used to produce scFv fragments, to about 5 amino acids. These linkers favor intrachain assembly of the VH and VL domains. Any suitable short linker can be used. Thus, two fragments assemble into a dimeric molecule. Further reduction of the linker length to 0-2 amino acids can generate trimeric (triabodies) or tetrameric (tetrabodies) molecules.

For preparation of antibodies, e.g., recombinant, monoclonal, or polyclonal antibodies, many techniques known in the art can be used (see, e.g., Kohler & Milstein, *Nature* 256:495-497 (1975); Kozbor et al., *Immunology Today* 4:72 (1983); Cole et al., in *Monoclonal Antibodies and Cancer Therapy*, Alan R. Liss, Inc., pp. 77-96 (1985); Coligan, *Current Protocols in Immunology* (1991); Harlow & Lane, Antibodies, *A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3rd ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625, 126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; and WO 92/200373).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Using Antibodies, A Laboratory Manual* (1998) for a description of immunoassay formats and conditions that can be used to determine specific immunoreactivity).

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity, neurodegeneration or pathological inflammation, normal human cells or tissues.

An "immunoregulator" refers to a substance, an agent, a signaling pathway or a component thereof that regulates an immune response. "Regulating," "modifying" or "modulating" an immune response refers to any alteration in a cell of the immune system or in the activity of such cell. Such regulation includes stimulation or suppression of the immune system which may be manifested by an increase or decrease in the number of various cell types, an increase or decrease in the activity of these cells, or any other changes which can occur within the immune system. Both inhibitory and stimulatory immunoregulators have been identified, some of which may have enhanced function in the cancer, infectious disease or neurodegenerative microenvironment.

The term "immunotherapy" refers to the treatment of a subject afflicted with, or at risk of contracting or suffering a recurrence of, a disease by a method comprising inducing, enhancing, suppressing or otherwise modifying an immune response. "Treatment" or "therapy" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication, condition or biochemical indicia associated with a disease.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

A "predetermined threshold value," relating to cell surface PD-L1 expression, refers to the proportion of cells in a test tissue sample comprising tumor cells and tumor-infiltrating inflammatory cells above which the sample is scored as being positive for cell surface PD-L1 expression. For cell surface expression, the predetermined threshold value for cells expressing PD-L1 on the cell surface ranges from at least about 0.01% to at least about 20% of the total number of cells. In preferred embodiments, the predetermined threshold value for cells expressing PD-L1 on the cell surface ranges from at least about 0.1% to at least about 10% of the total number of cells. More preferably, the predetermined threshold value is at least about 5%. Even more preferably, the predetermined threshold value is at least about 1%.

Construction of suitable vectors containing the desired sequences and control sequences employs standard ligation and restriction techniques, which are well understood in the art (see Maniatis et al., in *Molecular Cloning: A Laboratory Manual*, Cold Spring Harbor Laboratory, New York (1982)). Isolated plasmids, DNA sequences, or synthesized oligonucleotides are cleaved, tailored, and re-ligated in the form desired.

Nucleic acid is "operably linked" when it is placed into a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by readthrough transcription are also encompassed by this definition. Any products of a splicing reaction, including recombinant forms of the splice products, are included in this definition. An example of potassium channel splice variants is discussed in Leicher et al., *J. Biol. Chem.* 273(52):35095-35101 (1998).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

"Cancer" refers to human cancers and carcinomas, sarcomas, adenocarcinomas, etc., including solid tumors, kidney, breast, lung, kidney, bladder, urinary tract, urethra, penis, vulva, vagina, cervical, colon, ovarian, prostate, pancreas, stomach, brain, head and neck, skin, uterine, testicular, esophagus, and liver cancer.

In any of the embodiments above, one or more cancer therapies, e.g., chemotherapy, radiation therapy, immunotherapy, surgery, or hormone therapy can be co-administered further with the antibody of the invention.

In one embodiment, the chemotherapeutic reagent is an alkylating agent: nitrogen mustards, nitrosoureas, tetrazines, aziridines, cisplatins and derivatives, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Cisplatin and derivatives include cisplatin, carboplatin and oxaliplatin. In one embodiment the chemotherapeutic reagent is an anti-metabolites: the anti-folates (e.g., methotrexate), fluoropyrimidines (e.g., fluorouracil and capecitabine), deoxynucleoside analogues and thiopurines. In another embodiment the chemoptheraputic reagent is an anti-microtubule agent such as vinca alkaloids (e.g., vincristine and vinblastine) and taxanes (e.g., paclitaxel and docetaxel). In another embodiment the chemotherapeutic reagent is a topoisomerase inhibitor or a cytotoxic antibiotic such as doxorubicin, mitoxantrone, bleomycin, actinomycin, and mitomycin.

The contacting of the patient with the antibody or antibody fragment, can be by administering the antibody to the patient intravenously, intraperitoneally, intramuscularly, intratumorally, or intradermally. In some embodiments the antibody is co-administered with a cancer therapy agent.

"Neurodegenerative disease" refers to the progressive loss of structure or function of neurons, including death of neurons. Many neurodegenerative diseases including amyotrophic lateral sclerosis (ALS), Parkinson's disease, Alzheimer's disease, and Huntington's chorea occur as a result of neurodegenerative processes. Examples include, but are not limited to, Alzheimer's disease, other dementias such as frontotemporal dementia or vascular dementia, mild cognitive impairment, stroke, focal ischemia associated dementia, ALS, Parkinson's disease, and Huntington's chorea.

"Infectious disease" refers to bacterial, protozoan, and viral pathogens that infect humans and cause disease. Viral pathogens include human immunodeficiency virus, hepatitis B virus, hepatitis C virus, herpes virus. Bacterial and protozoal pathogens can include *E. coli*, *Staphylococcus* sp., *Streptococcus* sp., *Mycobacterium tuberculosis*, *Giardia*, *Malaria*, *Leishmania*, and *Pseudomonas aeruginosa*.

An infectious pathogen can be a capable of establishing chronic infections, e.g., those that are prolonged or persistent.

The term "refolding" as used herein refers to the process by which a protein structure assumes its functional shape or conformation. It is the physical process by which a polypeptide folds into its characteristic and functional three-dimensional structure from random coil. It takes place at a basic pH (typically pH 8.0-10.0, pH 8.5-10, or pH 8.5-9.6), a low temperature (typically 0.0° C. to 10.0° C. or 2.0° C. to 8.0° C.), preferably with the presence of a redox pair at suitable concentrations, and/or at the presence of oxygen, and/or at the presence of catalyst(s) such as copper ions at suitable concentration.

The term "recombinant" as used herein refers to a polypeptide produced through a biological host, selected from a mammalian expression system, an insect cell expression system, a yeast expression system, and a bacterial expression system.

The term "formulation" as used herein refers to the antibodies disclosed herein and excipients combined together which can be administered and has the ability to bind to the corresponding receptors and initiate a signal transduction pathway resulting in the desired activity. The formulation can optionally comprise other agents.

The present specification also provides a pharmaceutical composition for the administration to a subject. The pharmaceutical composition disclosed herein may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition disclosed herein, and other factors known in medicine.

The pharmaceutical composition including the antibody disclosed herein may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The disclosed compositions may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include, without limitation, lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methyl hydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

The composition may be formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The composition may be used by blending with a variety of pharmaceutically acceptable carriers such as physiological saline or organic solvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition disclosed herein are determined by the type of active ingredient, together with various factors such as the disease to be treated, administration route, patient's age, gender, and body weight, and disease severity.

The total effective dose of the compositions disclosed herein may be administered to a patient in a single dose, or may be administered for a long period of time in multiple doses according to a fractionated treatment protocol. In the pharmaceutical composition disclosed herein, the content of active ingredient may vary depending on the disease severity. Preferably, the total daily dose of the peptide disclosed herein may be approximately 0.0001 μg to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows suitable effects.

Moreover, the pharmaceutical composition may be administered alone or in combination or coincident with other pharmaceutical formulations showing prophylactic or therapeutic efficacy.

In still another aspect, the present specification provides a method for preventing or treating of cancer, infectious diseases or neurodegenerative diseases comprising the step of administering to a subject the chimeric protein or the pharmaceutical composition including the same.

As used herein, the term "prevention" means all of the actions by which the occurrence of the disease is restrained or retarded.

As used herein, the term "treatment" means all of the actions by which the symptoms of the disease have been alleviated, improved or ameliorated. In the present specification, "treatment" means that the symptoms of cancer, neurodegeneration, or infectious disease are alleviated, improved or ameliorated by administration of the antibodies disclosed herein.

As used herein, the term "administration" means introduction of an amount of a predetermined substance into a patient by a certain suitable method. The composition disclosed herein may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

In the present specification, the term "subject" is those suspected of having or diagnosed with cancer, a neurodegenerative or an infectious disease. However, any subject to be treated with the pharmaceutical composition disclosed herein is included without limitation.

The pharmaceutical composition including the anti-PD-L1 antibody disclosed herein is administered to a subject suspected of having cancer, a neurodegenerative or an infectious disease.

The therapeutic method of the present specification may include the step of administering the composition including the antibody at a pharmaceutically effective amount. The total daily dose should be determined through appropriate medical judgment by a physician, and administered once or several times. The specific therapeutically effective dose level for any particular patient may vary depending on various factors well known in the medical art, including the kind and degree of the response to be achieved, concrete compositions according to whether other agents are used therewith or not, the patient's age, body weight, health condition, gender, and diet, the time and route of administration, the secretion rate of the composition, the time period of therapy, other drugs used in combination or coincident with the composition disclosed herein, and like factors well known in the medical arts.

In still another aspect, the present specification provides a use of the therapeutic protein or the pharmaceutical composition including the same in the preparation of drugs for the prevention or treatment of cancer, a neurodegenerative or an infectious disease.

In one embodiment, the dose of the composition may be administered daily, semi-weekly, weekly, bi-weekly, or monthly. The period of treatment may be for a week, two weeks, a month, two months, four months, six months, eight months, a year, or longer. The initial dose may be larger than a sustaining dose. In one embodiment, the dose ranges from a weekly dose of at least 0.01 mg, at least 0.25 mg, at least 0.3 mg, at least 0.5 mg, at least 0.75 mg, at least 1 mg, at least 1.25 mg, at least 1.5 mg, at least 2 mg, at least 2.5 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 50 mg, at least 55 mg, at least 60 mg, at least 65 mg, or at least 70 mg. In one embodiment, a weekly dose may be at most 0.5 mg, at most 0.75 mg, at most 1 mg, at most 1.25 mg, at most 1.5 mg, at most 2 mg, at most 2.5 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 50 mg, at most 55 mg, at most 60 mg, at most 65 mg, or at most 70 mg. In a particular aspect, the weekly dose may range from 0.25 mg to 2.0 mg, from 0.5 mg to 1.75 mg. In an alternative aspect, the weekly dose may range from 10 mg to 70 mg.

EXAMPLES

Antibody Methods

Rabbit Immunization:

Female NZW rabbits (Prosci Inc., Poway, Calif. and R & R Research, Stanwood, Wash.) were immunized subcutaneously with 200 ug human PD-L1-his (Acrobiosystems cat. #PD1-H5221) in an equal volume of Sigma adjuvant (Sigma-Aldrich cat. #S6322) on day 0. Animals were boosted with antigen and adjuvant on day 21 and 42, and whole blood was collected in EDTA for B cell cloning 10 days after each boost. Subsequent boosts were performed at least 21 days apart using 100-200 ug human and/or murine PD-L1-his (Acrobiosystems cat. #PD1-M5220) in Sigma Adjuvant.

B-Cell Cloning:

Complete medium RPMI 1640 (Life Technologies, cat. #11875-119), 10% fetal bovine serum (Sciencell, cat. #0500), non-essential amino acids (Life Technologies, cat. #11140-050), sodium pyruvate (Life Technologies, cat.

11360-070), 2-mercaptoethanol (Life Technologies, cat. #21-985-023), and gentamicin (Life Technologies, cat. #15710-072).

Preparation of Rabbit Spleen/Thymus Conditioned Medium:

Rabbit thymocytes (Spring Valley Labs, Woodbine, Md.) at $2\times10^6$/mL were cultured with $2\times10^6$/mL rabbit splenocytes (Spring Valley Labs, Woodbine, Md.) in complete medium containing 10 ng/mL PMA (Sigma-Aldrich, cat. #P1585) and 0.5% PHA-m (ThermoFisher, cat. #10576-015) for 48 hours. Supernatant was 0.2 uM filtered and stored at −20° C.

B Cell Cloning:

Approximately 25 mL of whole rabbit blood was collected in EDTA 10 days after an antigen boost. Blood was layered over 15 mL of Lymphoprep (Accurate Chemical, cat. #AN1001969) in a 50 cc polypropylene centrifuge tube. Blood was then centrifuged at 2000 rpm for 25 minutes. Peripheral blood mononuclear cells (PBMC) were collected from the gradient interface, and washed 3 times with 50 mL PBS.

A 60 mm petri dish was coated with 3 mL human PD-L1-his at 2 ug/mL in PBS and incubated overnight at 4° C. Coating solution was removed and 3 mL PBS/5% BSA was added to block at room temperature for 1-2 hours. The blocking solution was removed and the plate was washed 4 times with PBS. Rabbit PBMC were added to the plate in 3 mL PBS/2.5% BSA, and incubated for 45 minutes at 4° C. The dish was then washed 5 times with PBS/BSA to remove non-adherent cells, and then the adherent cells were harvested into complete medium by scraping with a cell scraper.

Cells were then plated into 96 well round-bottom plates at 10-200 cells/well in complete medium containing 2% rabbit spleen/thymus conditioned medium, human IL-2 (Prospec, cat. #cyt-095) at 5-10 ng/mL, Pansorbin (EMD Millipore, cat. #507858) at 1:20,000, and $5\times10^4$ mitomycin-c (Sigma-Aldrich, cat. #M4284) treated (50 ug/mL for 45 minutes) EL4-B5 cells/well. Plates were incubated for 7 days at 37° C. in $CO_2$ incubator, supernatants were removed for assay, and plates containing the cells were frozen at −80° C. for subsequent antibody v-region rescue.

Transient Transfection:

Confirmation of successful v-region rescue was done by transfecting the heavy and light chains into HEK293 cells and testing the supernatant for recovery of PD-L1 binding activity.

HEK293 cells were plated at $1.5\times10^5$ cells/well in 1 mL complete medium in a 24 well tissue culture plate, and cultured overnight. Transfection was performed using 500 ng heavy chain DNA and 500 ng light chain DNA with Lipofectamine 3000 (Life Technologies, cat. #L3000015) per manufacturer's instructions. Supernatants were harvested after 3-5 days and assayed for binding activity by ELISA.

Larger scale transfections to generate material for purification were performed with HEK293 cells cultured in 5% ultra-low IgG fetal bovine serum (Life technologies, cat. #16250-078) using Lipofectamine 3000 per manufacturer's instructions.

Analytical Assays for Screening and for Characterization of mAb

PD-L1 Binding ELISAs:

B cell cloning supernatants were tested for binding to PD-L1 by ELISA. ELISA plates were coated with 100 uL antigen at 0.5 or 1 ug/mL in PBS (Life Technologies, cat. #14190-250) overnight at 4° C. or for 1 hour at 37° C. Antigens tested include; human PD-L1-Fc (Acrobiosystems, cat. #PD1-5257), human PD-L1-his, murine PD-L1-his. Plates were then blocked with PBS+10% goat serum for 1 hour. After washing with deionized water, samples were added in PBS/10% goat serum and incubated for 1 hour. Plates were washed, and 100 uL goat anti-rabbit IgG Fc-HRP (Jackson ImmunoResearch, cat. #111-035-046) was added at a 1:5000 dilution in PBS/10% goat serum for 1 hour. Plates were then washed with deionized water and 100 uL TMB substrate (Thermo Scientific, cat. #PI134021) was added to each well. Development was stopped with 100 uL 1N $H_2SO_4$, and $OD_{450}$ was measured using a microplate spectrophotometer. FIGS. 1 and 2 show the examples from the screening ELISA analysis of the B cell cloning supernants.

Purified chimeric and humanized antibodies were tested for binding to PD-L1 by ELISA. Antigens tested include; human PD-L1-Fc, human PD-L1-his, murine PD-L1-his, and cynomolgus PD-L1-his (Sinobiological, cat. #90251-C08H) and human PDL2 (Acrobiosystems, cat. #PD2-H5251). Protocols were the same as for testing B cell cloning supernatants except that the secondary antibodies were as follows; for human PD-L1-Fc the secondary was goat anti-human kappa-HRP (Novex, Life Technologies, cat. #A18853), for human PD-L1-his, murine PD-L1-his and cynomolgus PD-L1-his the secondary was goat anti-human IgG Fc-HRP (Jackson ImmunoResearch, cat. #109-005-098). FIG. 3 shows the binding of the purified PD-L1 antibodies to PD-L1 as analyzed by binding ELISA.

Competition ELISA:

Purified chimeric and humanized anti-PD-L1 antibodies were tested for their ability to block PD-L1 binding to the receptor PD1.

ELISA plates were coated with 100 uL human PD-L1-Fc at 1 ug/mL in Carbonate buffer pH 9.6 overnight at 4° C. or for 1 hour at 37° C. Plates were washed twice with TBST (50 mM Tris HCl, pH 7.4, 150 mM NaCl, 0.1% Tween). Plates were blocked with 150 uL/well TBST/2% BSA, and incubated 1.5 hours at 37° C. Plates were washed twice with TBST. Anti-PD-L1 antibodies were added in 50 uL/well TBST/0.5% BSA and incubated 30 minutes at 37° C. PD1-his was then added in 50 uL at 25 ug/mL in PBS/0.5% BSA, and the plates incubated for 1 hour at 37° C. Plates were washed 5 times with TBST and 100 uL/well anti-His-HRP (Rockland, cat. #200-303-382) was added at 1:5000 in TBST/0.5% BSA and incubated for 1 hour at 37° C. Plates were washed 6 times with TBST, and 100 uL/well TMB substrate was added. Development was stopped with 100 uL/well 1N H2504, and $OD_{450}$ was measured with a microplate spectrophotometer. FIG. 4 shows the results of several antibodies in their abilities of blocking the binding of PD-L1 to PD-1.

SEB Assay:

Purified anti-PD-L1 antibodies were tested for their ability to enhance IL-2 secretion from whole blood treated with staphylococcus enterotoxin B (SEB).

Heparinized whole blood is diluted 1:5 with RPMI 1640+ gentamicin and SEB (List Biological, cat. #122) is added to 0.2 ug/mL. Serial 3-fold dilutions of PD-L1 antibodies are made starting at 10 ug/mL (final concentration after addition of whole blood) in 100 uL/well RPMI, gentamicin, and 1% autologous plasma. Diluted whole blood is then added at 100 uL/well, and plates are incubated for 4 days at 37° C. in 5% $CO_2$. Supernatant is then collected for measurement of IL-2 secretion by ELISA.

IL-2 ELISA: Plates were coated with 100 uL mouse anti-human IL-2 (B-D Pharmingen, cat. #555051) at 2 ug/mL in PBS overnight at 4° C. or 1 hour at 37° C. Add 100 uL/well PBS/10% goat serum to block. Incubate 1 hour. Plates were washed with deionized water. Samples and standards were added in 100 uL/well PBS/10% goat serum and incubated for 1 hour. After washing with deionized water, 100 uL/well anti-human IL-2 biotin (B-D Pharmingen, cat. #5550400) was added at 1 ug/mL in PBS 10% goat serum, and incubated for 1 hour. Plates were washed with deionized water and 100 uL streptavidin-HRP (Jackson ImmunoResearch, cat. #016-030-084) was added at 1:1000 in PBS/10% goat serum. After 1 hour incubation plates were washed with deionized water, and 100 uL/well TMB substrate was added to each well. Development was stopped with 100 uL 1N $H_2SO_4$ and $OD_{450}$ was measured using a microplate spectrophotometer.

FIG. 5 shows the examples of several cloned PD-L1 antibodies in their abilities in promoting IL-2 secretion.

MLR:

Purified anti-PD-L1 antibodies were tested for their ability to enhance interferon gamma (IFN-gamma) secretion in a mixed lymphocyte reaction (MLR). In this assay dendritic cells from one donor are mixed with CD3+ cells from a second donor with and without anti-PD-L1. In the presence of PD1/PD-L1 antagonists IFN-gamma secretion is enhanced.

Generation of dendritic cells: PBMC were purified from buffy coats (Research Blood Components, Boston, Mass.). Buffy coats were diluted 1:3 in PBS and layered over 15 mL cushions of Lymphoprep in 50 mL tubes and centrifuged at 2000 rpm for 25 minutes. PBMC were collected from the gradient interface, and washed 3 times with PBS. PBMC are then cultured in tissue culture flasks at approximately 1-2× $10^6$ cells/cm$^2$ in RPMI 1640+1% fetal bovine serum. Incubate 1-1.5 hours at 37° C. Wash cells 2 times with serum free RPMI 1640 to remove non-adherent cells. Culture adherent cells in complete medium+30 ng/mL human GM-CSF (Prospec, cat. #cyt-221) and 10 ng/mL human IL-4 (Prospec, cyt-271) for 7 days.

Generation of CD3+ cells: From a second donor PBMC were purified from buffy coats and adhered in tissue culture flasks as described previously. Non-adherent cells were collected and re-suspended in MACS buffer (PBS, 2 mM EDTA, 0.5% fetal bovine serum). CD3+ cells were purified using MACS anti-CD3 beads (Miltenyi Biotec, Cologne, Germany. Cat #130-050-101) per manufacturer's instructions.

Serial dilutions of anti-PD-L1 were performed in 96 well plates in complete medium, and 10,000 dendritic cells with 100,000 CD3+ cells were added to each well. Cultures were incubated for 5 days, and the supernatant was assayed for Interferon-gamma Interferon-Gamma ELISA:

Plates were coated with 100 uL mouse anti-human IFN-gamma (Biolegend, cat. #507502) at 1 ug/mL in PBS overnight at 4° C. or 1 hour at 37° C. Add 100 uL/well PBS/10% goat serum to block. Incubate 1 hour. Plates were washed with deionized water. Samples and standards were added in 100 uL/well PBS/10% goat serum and incubated for 1 hour. After washing with deionized water, 100 uL/well anti-human IFN-gamma biotin (Biolegend, cat. #5002504) was added at 1 ug/mL in PBS 10% goat serum, and incubated for 1 hour. Plates were washed with deionized water and 100 uL streptavidin-HRP (Jackson ImmunoResearch, cat. #016-030-084) was added at 1:1000 in PBS/10% goat serum. After 1 hour incubation plates were washed with deionized water, and 100 uL/well TMB substrate was added to each well. Development was stopped with 100 uL 1N $H_2SO_4$ and $OD_{450}$ was measured using a microplate spectrophotometer.

FIG. 6 shows the examples of PD-L1 antibodies in their abilities of promoting interferon gamma secretion.

Flow Cytometry:

Binding of candidate anti-PD-L1 antibodies to cell surface expressed PD-L1 was measured using flow cytometry.

Generation of stable human PD-L1 expressing HEK293 cells: HEK293 cells were seeded in one well of a 6 well plate in complete medium and cultured overnight. The culture medium was removed, and 2 mL of fresh complete medium containing 8 ug/mL polybrene (Santa Cruz Biotechnology, cat. #sc-134220) was added. Human PD-L1 lentiviral particles (G & P Biosciences, cat. #LTV-PD-L1-puro) were added in 0.5 mL. After overnight culture, PD-L1+ cells were selected in puromycin (Life Technologies, cat. #A1113803).

Figure 7:
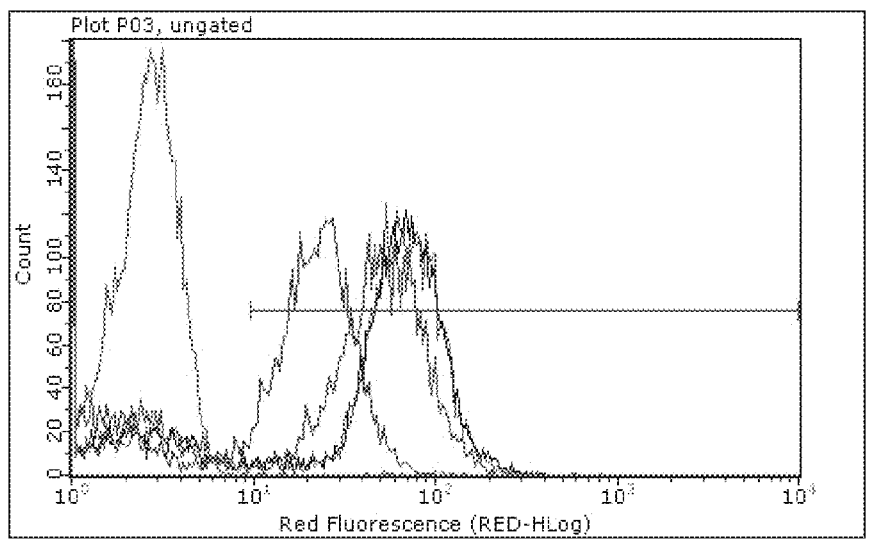
FIG. 7. Example of chimeric anti-PD-L1 mAbs binding to cell surface PD-L1 on HEK293 cells stably transduced with human PD-L1. Anti-PD-L1 mAbs show no binding to parental HEK293.

Cells to be analyzed were incubated at 0.5-1×$10^6$ cells in 50 uL PBS/10% goat serum/0.02% sodium azide for 10 minutes. Anti-PD-L1 or control antibodies were added at 4 ug/mL in 50 ug/mL FACS buffer (PBS/1% fetal bovine serum/0.2% sodium azide) and incubated for 15 minutes at 4° C. Cells were washed with FACS buffer, and re-suspended in 100 uL goat anti human IgG-PE (eBioscience, cat. #12-4998) at 1 ug/mL in FACS buffer, and incubated for 15 minutes for at 4° C. Cells were then washed with FACS buffer and analyzed using a Guava flow cytometer (EMD Millipore). Results in FIG. 7 are shown examples to demonstrate the binding of several of the antibodies binding to the PD-L1 expressed on cell surfaces.

Figure 8:
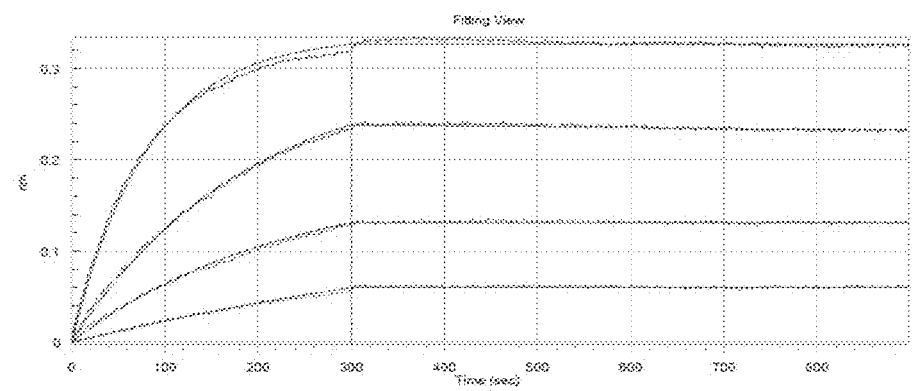
FIG. 8. Example of Affinity measurement for mAb using Octet.

Affinity Measurement:

The affinity measurement was conducted with Octet RED 96 (ForteBio) instrument at 30 degree Celsius. Briefly, anti-human IgG capture sensor (AHC from ForteBio cat #18-5060) was equilibrated with assay buffer (1× dilution of 10× Kinetics Buffer (ForteBio, Cat #18-5032). Test antibody samples were diluted to 3 ug/mL and allowed to bind to the sensors for 5 min. The sensors were then washed in assay buffer for 3 minutes, and PD-L1 ligand diluted at different concentrations were allowed to bind to the mAb coated on the sensors for 5 minutes. Afterwards, dissociation was followed for 10 minutes in the assay buffer. The sensors could be regenerated by washing in glycine buffer and assay buffer 3 times. The data were fitted with 1:1 binding model using the ForteBio software. An example of the affinity measurement is given in FIG. 8.

PD1/PD-L1 Blockade Reporter Assay:

The ability of anti-PD-L1 antibodies to block PD-L1 mediated PD1 signaling was measured using two engineered cell lines. The first is a CHO-K1 cell line (CHO-K1/TCRA/PD-L1, BPS Bioscience cat #60536) expressing both human PD-L1 and a T cell receptor activator. The second cell line (PD1/NFAT, BPS Bioscience cat #60535) is a Jurkat T cell line expressing PD1 and an NFAT firefly luciferase reporter. The T cell receptor activator on the CHO-K1 cells will activate the Jurkat cells resulting in expression of the NFAT luciferase reporter. However, since the CHO-K1 cells also express PD-L1, signaling via PD1 results in inhibition of NFAT activation. Blocking the PD-L1/PD1 interaction will restore NFAT activation and luciferase activity.

Figure 9:
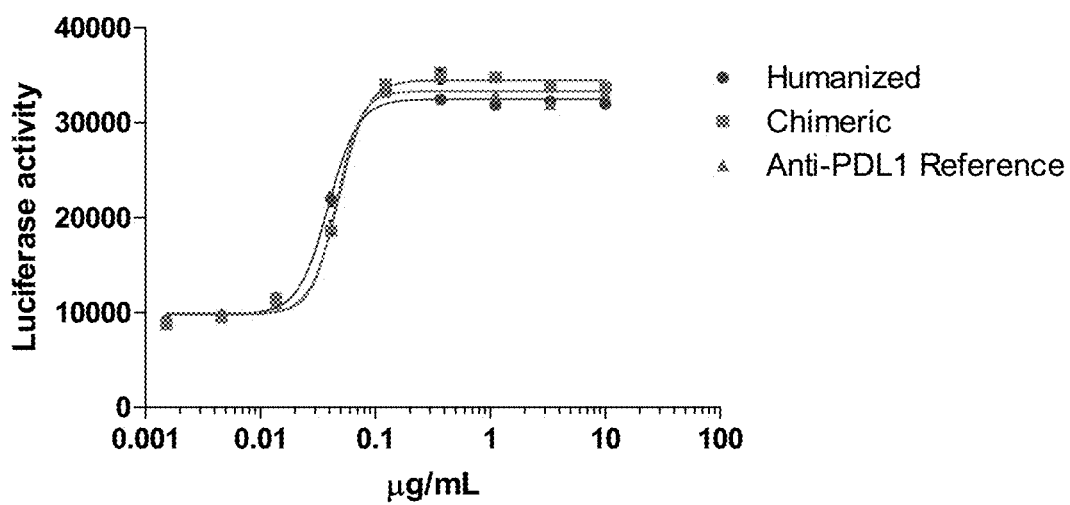
FIG. 9. Reporter assays showing ability of the chimeric and humanized anti-PD-L1 111H2 antibodies to block PD-L1 mediated PD1 signaling.

CHO-K1/TCRA/PD-L1 cells are seeded in 96 well flat bottom plates at 35,000 cells/well in 100 uL assay medium (RPMI 1640, 10% Fetal Bovine serum, Non-essential amino acids, 2-mercaptoethanol, and gentamicin) in 96 well white walled, flat bottom plates. After overnight culture, the culture medium is removed and samples and standards are added at 2× concentration in 50 uL/well. Plates are incubated 20 minutes, and 20,000 PD1/NFAT cells are added to each well in 50 uL. Plates are incubated 6 hours at 37° C. Plates are cooled to room temperature for 5 minutes, and 100 uL/well luciferase reagent (Pierce Firefly Luc One-Step Glow Assay Kit, Thermo Scientific cat #16197) is added. Plates are incubated for 15 minutes, then luminescence is measured on a luminometer. An example of the reporter assay is given in FIG. 9.

V-Region Rescue from Rabbit B-Cells and Screening of Chimeric Antibodies

To rescue rabbit B-cells that were tested positive for PD-L1 binding, the IgG variable domain for both the heavy and light chains were captured by amplification using reverse transcriptase coupled polymerase chain reaction (RT-PCR) from mRNA isolated from positive B-cells. The VH and VL cDNAs thus obtained, were cloned and ligated onto human constant region constructs, such that the final cDNA construct encoded a chimeric rabbit human IgG.

Selected positive B-cells were lysed and mRNA prepared using the Dynabeads mRNA DIRECT Micro Kit, from Life Technologies according to the manufacturer's instructions.

To recover the v-regions, mRNA generated from a single antigen positive well is used in a OneStep RT-PCR Kit (Qiagen) reaction for both the heavy and light chains according to the manufacturer's instructions. For the reactions, gene specific primers located in the constant regions of the heavy and light chains of the rabbit IgG molecule are used to generate a single strand cDNA, followed PCR and nested PCR to amply the variable domains with specific restriction sites added to the ends of PCR products. In-house vectors containing constant gamma-1 heavy and constant kappa light chain human regions with specific restriction sites were used for subcloning. After addition of the restriction sites, the PCR products were subjected to the relevant Restriction enzymes digestion, gel purified and ligated into the appropriate vector.

Following sub cloning, the ligated DNA was transformed into competent DH5 *E. coli* (Invitrogen). The entire transformation pool was cultured over-night in medium containing the appropriate antibiotic resistance. The cultured bacteria were split into two parts: one part for making plasmid DNA prep (Qiagen kit) for use in transient HEK293 expression of chimeric antibodies, and the other part saved for plating single colonies for DNA sequencing.

To generate the chimeric antibodies, HEK293 cells were co-transfected with the DNA of both heavy and light chain from a selected well. Supernatant was harvested after three to five days of cell culture and assayed for IgG and antigen binding by ELISA. To detect the presence of IgG in the transfection supernatant, an ELISA immunoassay is done which utilizes an anti-human IgG Fc capture antibody coated to an ELISA plate, followed by the supernatants and human IgG standard. Detection of Fc-captured antibody is obtained using an anti-human IgG (H&L)-HRP reagent and TMB substrate.

The isolated DNA preps that gave positive chimeric antibody expression and antigen binding functions were processed for DNA sequencing. It should be note that the isolated DNA plasmids at this stage may or may not be homogenous for one specific V-region, as selected wells may contain one or more different B-cell clones. To break the pool into single clones, $DH_{alpha}$ *E. coli* culture pool from which the DNA was isolated previously was plated to single colonies on agar plate containing the appropriate antibiotic. Multiple colonies were picked and processed for DNA production using a rolling circle DNA amplification kit (Templiphy, GE Healthcare) following manufacturer's instructions. The DNA generated from the Templiphy reactions was sequenced and subsequently analyzed to determine the complexity of V-regions for each well. In addition to making DNA, each clone of bacteria used for the Templiphy reaction was saved for future DNA isolation.

Based on the DNA sequence analysis, plasmid DNA preps were made from the corresponding single clone *E. coli* culture containing the unique IgG heavy chain or light Chain sequences. These plasmids were then used to transform HEK293 again to screen for chimeric monoclonal antibody. In case that there were multiple heavy and light chain sequences obtained from the same B-cell well (wells not clonal), every possible combination of unique heavy and light chain pairs was transfected. Supernatants were harvested after three to five days, assayed for IgG and antigen binding by ELISA. After this deconvolution step, heavy and light chain combinations which retained the desired binding activity were selected for further functional analysis and then for humanization.

Properties and Sequence Information for Top Antibody Candidates

The top nine antibodies with unique DNA sequences were characterized with the purified chimeric proteins. The results are summarized in Table 1.

TABLE 1

Characterization of Top Chimeric mAbs

| Clone | HC | LC | $K_{on}$ (1/Ms) | $K_{off}$ (1/s) | KD (pM) | SEB Functional Assay | Specificity Blocking PD-L1/PD1 binding | Binding to cell Surface PD-L1 | Binding to monkey PD-L1 | Binding to mouse PD-L1 | Binding to human PD-L2 |
|---|---|---|---|---|---|---|---|---|---|---|---|
| 111F1 | 4 | 1 | $7.69 \times 10^5$ | $6.2 \times 10^{-5}$ | 162 | + | + | + | + | − | − |
| 110B4 | 3 | 2 | $4.04 \times 10^5$ | $6.87 \times 10^{-5}$ | 173 | + | + | + | + | − | − |
| 115E2 | 1 | 1 | $5.32 \times 10^5$ | $4.99 \times 10^{-5}$ | 100 | + | + | + | + | − | − |
| 116F3 | 1 | 4 | $6.82 \times 10^5$ | $<1 \times 10^{-7}$ | <1 | + | + | + | + | − | − |
| 113F1 | 2 | 6 | $3.62 \times 10^5$ | $3.78 \times 10^{-5}$ | 115 | + | + | + | + | − | − |
| 113G3 | 2 | 1 | $3.33 \times 10^5$ | $1.85 \times 10^{-5}$ | 51 | + | + | + | + | − | − |
| 115C1 | 1 | 1 | $4.55 \times 10^5$ | $2.08 \times 10^{-5}$ | 51 | + | + | + | + | − | − |
| 111H2 | 1 | 6 | $1.07 \times 10^6$ | $1.97 \times 10^{-4}$ | 183 | + | + | + | + | − | − |
| 110H8 | 1 | 1 | $7.55 \times 10^5$ | $<1 \times 10^{-7}$ | <1 | + | + | + | + | − | − |

The variable domain rabbit protein sequences of the top nine chimeric antibodies are provided in Table 2 (HC) and Table 3 (LC), and the CDR for each top candidate are provided Tables 4-12.

TABLE 2

HC Variable Domain Protein Sequences

| Clone | SEQ ID Number | HC variable domain Protein Sequence |
|---|---|---|
| 111F1 | 1 | cqsvkesegglfkptdtltltctvsgidlnsiais wvrqapgnglewigtigssgsayyaswaksrstit rntsentvtlemtsltaadtatyfcakeilyygmd lwgpgtlvtvss |
| 110B4 | 2 | cqsvkesegglfkptdtltlckvsgidlssisisw vrqapgnglewigvinsygntyyaswaksrstitr ntnentvtlkmtsltaadtatyfcakeilyygmdl wgpgtlvtvss |
| 115E2 | 3 | cqsvkesegglfkpmdtltltctvsgidlgsvais wvrqapgkglewigtigssgsayyaswaksrstit rntnlntvtlkmtsltaadtasyfcakeilyygmd rwgpgtlvtvss |
| 116F3 | 4 | cqsvkesegglfkptdtltltctvsgidlssisig wvrqapgnglewigtisdsgsayyaswaksrstit rntnentvtlkmtsltaadtatyfcakeilyygmd lwgpgtlvtvss |
| 113F1 | 5 | cqsvkesegglfkptdtltltctvsgidlssiais wvrqapgnglewigtinsygstyyaswaqsrstit rntnentvtlkmtsltaadtatyfcakeilyygmd vwgpgtlvtvss |
| 113G3 | 6 | cqsvkesxgglfkptdtltltctvsgfslssvavs wvrqapgnglewigtisytgttyyaswaksrstit rntdentvtlkmpsltvadtatyfcakeilyygmd fwgpgtlvtvss |
| 115C1 | 7 | cqsvkesegglfkptdtltltctvsgfslssvavs wvrqapgkglewigtisytgntyyaswaksrstit rntnentvtlkmpsltvadtatyfcakeilyygmd fwgpgtlvtvss |
| 111H2 | 8 | cqeqlvesgggvqpggtlklsckgsgfdlssnam cwvrqapgkglewigcivygncyyaswvngrftis sdnaqssvdlqlnsltaadtatyfcardpagssvy tggfniwgpgtlvtvss |
| 110H8 | 9 | cqsvkesegglfkptdtltlctvsgidlssvsisw vrqapgnglewigtigasgsayyaswakrrstitr ntnlntvtlkmtsltaadtasyfcakeilyygmdl wgpgtlvtvss |

TABLE 3

LC Variable Domain Protein Sequences

| Clone | SEQ ID Number | LC variable domain Protein Sequence |
|---|---|---|
| 111F1 | 10 | dpvmtqtpasvsepvggtvtincqasqsissylaw yqqkpgqrpklliyaasnvepgvpsrfrgrsgtq ftltisdlecddaatyycqstygstgggdygnafg ggtkvvvvrt |
| 110B4 | 11 | dvvmtqtpasveaavggtvtikcqasqsissyfsw yqqkpgqrpklliydasnlesgvpsrfkgsrsgte ytltisdlewddaatyycqctygstsssnygnnfg ggtkvvvvrt |
| 115E2 | 12 | dvvmtqtpasveasvggtvtincqasqsissylaw yqqkpgqppklliyaasnlepgvpsrfkgsgsgte ftltisdlecadaatyycqatygstsssdygnafg ggtkvvvvrt |
| 116F3 | 13 | dvvmtqtpasvsgavggtvtikcqasediesylaw yqqkpgqppklliyaasnlepgvpsrfkgsrsgte ytltitdlecddaatyhcqatygstsssdygnafg ggtkvvvvrt |

TABLE 3-continued

LC Variable Domain Protein Sequences

| Clone | SEQ ID Number | LC variable domain Protein Sequence |
|---|---|---|
| 113F1 | 14 | dvvmtqtpasveaavggtvtikcqasqsissylaw yqqkpgqppklliyaasnlesgvpsrfkgsgsgte ytltisdlecddaatyycqstygttstsdygnafg ggtkvvvvrt |
| 113G3 | 15 | divmtqtpssvsaavggtvtincqasqsvsnllvw yqqkpgqppklliyaasnlesgvpsrfkgsgsgtd ftltisdlecadaatyycqstygststsdygnafg ggtkvvvvrt |
| 115C1 | 16 | divmtqtpssvsaavggtvtincqasqsissylaw yqqkpgqppklliyaasnlesgvpsrfkgsgsgtd ftltisdlecadaatyycqstygststdygnafgg gtkvvvvrt |
| 111H2 | 17 | aidmtqtpspvsaavgdtvtincqaseniysflaw yqqkpghspkpliyfasklasgvpsrfkgsgsgtq ftltisdvqcddaatyycqqtvsyknadtafgggt kvvvvrt |
| 110H8 | 18 | dvvmtqtpasveaavggtvtikcqasqsisnylaw yqqkpgqrpklliyaasnlepgvpsrfkgsgsgte ytltitdlecddaatyhcqctygstsssdygnafg ggtkvvvvrt |

TABLE 4

CDR for 116F3

| SEQ ID Number | Name | Sequence |
|---|---|---|
| 19 | CDR1 VH | SSISIG |
| 20 | CDR2 VH | TISDSGSAYYASWAKS |
| 21 | CDR3 VH | EILYYGMDL |
| 22 | CDR1 VL | QASEDIESYLA |
| 23 | CDR2 VL | AASNLEP |
| 24 | CDR3 VL | QATYGSTSSSDYGNA |

TABLE 5

CDR for 113G3

| SEQ ID Number | Name | Sequence |
|---|---|---|
| 25 | CDR1 VH | SSVAVS |
| 26 | CDR2 VH | TISYTGTTYYASWAKS |
| 27 | CDR3 VH | EILYYGMDF |
| 28 | CDR1 VL | QASQSVSNLLV |
| 29 | CDR2 VL | GASNLES |
| 30 | CDR3 VL | QSTYGSTSTSDYGNA |

TABLE 6

CDR for 115C1

| SEQ ID Number | Name | Sequence |
|---|---|---|
| 31 | CDR1 VH | SSVAVS |
| 32 | CDR2 VH | TISYTGNTYYASWAKS |
| 33 | CDR3 VH | EILYYGMDF |
| 34 | CDR1 VL | QASQSISSYLA |
| 35 | CDR2 VL | GASNLES |
| 36 | CDR3 VL | QSTYGSTSTSDYGNA |

TABLE 7

CDR for 110B4

| SEQ ID Number | Name | Sequence |
|---|---|---|
| 37 | CDR1 VH | SSISIS |
| 38 | CDR2 VH | VINSYGNTYYASWAKS |
| 39 | CDR3 VH | EILYYGMDL |
| 40 | CDR1 VL | QASQSISSYFS |
| 41 | CDR2 VL | DASNLES |
| 42 | CDR3 VL | QCTYGSTSSSNYGNN |

TABLE 8

CDR for 113F1

| SEQ ID Number | Name | Sequence |
|---|---|---|
| 43 | CDR1 VH | SSIAIS |
| 44 | CDR2 VH | TINSYGSTYYASWAQS |
| 45 | CDR3 VH | EILYYGMDV |
| 46 | CDR1 VL | QASQSISSYLA |
| 47 | CDR2 VL | AASNLES |
| 48 | CDR3 VL | QSTYGTTSTSDYGNA |

TABLE 9

CDR for 111F1

| SEQ ID Number | Name | Sequence |
|---|---|---|
| 49 | CDR1 VH | NSIAIS |
| 50 | CDR2 VH | TIGSSGSAYYASWAKS |
| 51 | CDR3 VH | EILYYGMDL |
| 52 | CDR1 VL | QASQSISSYLA |
| 53 | CDR2 VL | AASNVEP |
| 54 | CDR3 VL | QSTYGSTGGGDYGNA |

TABLE 10

CDR for 115E2

| SEQ ID Number | Name | Sequence |
|---|---|---|
| 55 | CDR1 VH | GSVAIS |
| 56 | CDR2 VH | TIGSSGSAYYASWAKS |
| 57 | CDR3 VH | EILYYGMDR |
| 58 | CDR1 VL | QASQSISSYLA |
| 59 | CDR2 VL | AASNLEP |
| 60 | CDR3 VL | QATYGSTSSSDYGNA |

TABLE 11

CDR for 111H2

| SEQ ID Number | Name | Sequence |
|---|---|---|
| 61 | CDR1 VH | SNAMC |
| 62 | CDR2 VH | CIVYGNCYYASWVNG |
| 63 | CDR3 VH | DPAGSSVYTGGFNI |
| 64 | CDR1 VL | QASENIYSFLA |
| 65 | CDR2 VL | FASKLAS |
| 66 | CDR3 VL | QQTVSYKNADTA |

TABLE 12

CDR for 110H8

| SEQ ID Number | Name | Sequence |
|---|---|---|
| 67 | CDR1 VH | SSVSIS |
| 68 | CDR2 VH | TIGASGSAYYASWAKR |
| 69 | CDR3 VH | EILYYGMDL |
| 70 | CDR1 VL | QASQSISNYLA |
| 71 | CDR2 VL | AASNLEP |
| 72 | CDR3 VL | QCTYGSTSSSDYGNA |

Humanization of Selected Chimeric Candidates

Four chimeric antibody candidates, 116F3, 113G3, 111H2, and 110H8 were selected for humanization. Several humanized variants for each candidate were designed based on sequence analysis, and then tested experimentally by creating the humanized mAb expression constructs and making the humanized mAb proteins from transient expression system. In addition, further optimization has been carried out to address the unpaired Cys in the VH of clone 111H2. The humanized mAb has human gamma-4 constant sequence (with S228P mutation for reducing half-antibodies) and human kappa constant sequence. The humanized sequences of the variable domains are provided in Tables 13-16. The sequences of the heavy chain and the light chain of a humanized antibody of Clone 111H2 (ASKB1296) are shown in Table 19.

In addition, the DNA sequences for the heavy chains and light chains for the humanized antibodies are listed in Table 17.

TABLE 13

Protein Sequences for Humanized 116F3 Variable Domains.

| SEQ ID | Variant Names | Sequence |
|---|---|---|
| 73 | VHV1 | QVQLQESGPGLVKPSETLSLTCTVSGIDLS SISIGWIRQPPGKGLEWIGTISDSGSAYYA SWAKSRVTISVDTSKNQFSLKLSSVTAADT AVYYCAREILYYGMDLWGQGTLVTVSSAS |
| 74 | VHV2 | QVQLQESGPGLVKPSETLSLTCTVSGIDLS SISIGWIRQPPGKGLEWIGTISDSGSAYYA SWAKSRVTISRDTSKNQFSLKLSSVTAADT AVYYCAREILYYGMDLWGQGTLVTVSSAS |
| 75 | VHV3 | QVQLQESGPGLVKPSETLSLTCTVSGGSLS SISIGWIRQPPGKGLEWIGTISDSGSAYYA SWAKSRVTISRDTSKNQFSLKLSSVTAADT AVYYCAREILYYGMDLWGQGTLVTVSSAS |
| 76 | VHV4 | EVQLLESGGGLVQPGGSLRLSCTVSGFTLS SISIGWVRQAPGKGLEWVSTISDSGSAYYA SWAKSRFTISRDNSKNTLYLQMNSLRAEDT AVYYCAKEILYYGMDLWGQGTLVTVSSAS |
| 77 | VHV5 | EVQLLESGGGLVQPGGSLRLSCAASGFTLS SISIGWVRQAPGKGLEWVSTISDSGSAYYA SWAKSRFTISRDNSKNTLYLQMNSLRAEDT AVYYCAKEILYYGMDLWGQGTLVTVSSAS |
| 78 | VKV1 | DIQMTQSPSSLSASVGDRVTITCQASEDIE SYLAWYQQKPGKAPKLLIYAASNLEPGVPS RFSGSGSGTDFTLTISSLQPEDFATYYCQA TYGSTSSSDYGNAFGGGTKVEIKRT |
| 79 | VKV2 | DIQMTQSPSSLSASVGDRVTITCQASEDIE SYLAWYQQKPGKAPKLLIYAASNLEPGVPS RFSGSRSGTDFTLTISSLQPEDFATYYCQA TYGSTSSSDYGNAFGGGTKVEIKRT |

TABLE 14

Protein Sequences for Humanized 113G3 Variable Domains

| SEQ ID | Variant Names | Sequence |
|---|---|---|
| 80 | VHV1 | EVQLLESGGGLVQPGGSLRLSCTVSGFSLS SVAVSWVRQAPGKGLEWVSTISYTGTTYYA SWAKSRFTISRDNSKNTLYLQMNSLRAEDT AVYYCAKEILYYGMDFWGQGTLVTVSS |
| 81 | VHV2 | EVQLLESGGGLVQPGGSLRLSCAASGFTLS SVAVSWVRQAPGKGLEWVSTISYTGTTYYA SWAKSRFTISRDNSKNTLYLQMNSLRAEDT AVYYCAKEILYYGMDFWGQGTLVTVSS |

TABLE 14-continued

Protein Sequences for Humanized 113G3 Variable Domains

| SEQ ID | Variant Names | Sequence |
|---|---|---|
| 82 | VHV3 | QVQLQESGPGLVKPSETLSLTCTVSGGSLS SVAVSWIRQPPGKGLEWIGTISYTGTTYYA SWAKSRVTISVDTSKNQFSLKLSSVTAADT AVYYCAKEILYYGMDFWGQGTLVTVSS |
| 83 | VHV4 | QVQLQESGPGLVKPSETLSLTCTVSGGSLS SVAVSWIRQPPGKGLEWIGTISYTGTTYYA SWAKSRVTISRDTSKNQFSLKLSSVTAADT AVYYCAKEILYYGMDFWGQGTLVTVSS |
| 84 | VHV5 | QVQLQESGPGLVKPSETLSLTCTVSGFSLS SVAVSWIRQPPGKGLEWIGTISYTGTTYYA SWAKSRVTISRDTSKNQFSLKLSSVTAADT AVYYCAKEILYYGMDFWGQGTLVTVSS |
| 85 | VKV1 | DIQMTQSPSSLSASVGDRVTITCQASQSVS NLLVWYQQKPGKAPKLLIYGASNLESGVPS RFSGSGSGTDFTLTISSLQPEDFATYYCQS TYGSTSTSDYGNAFGGGTKVEIK |

TABLE 15

Protein Sequences for Humanized 111H2 Variable Domain (see Table 18 below for additional sequences)

| SEQ ID | Variant Names | Sequence |
|---|---|---|
| 86 | VHV1 | EVQLVESGGGLVQPGGSLRLSCAASGFTLS SNAMCWVRQAPGKGLEWIGCIVYGNCYYAS WVNGRFTISRDNSKNTLYLQMNSLRAEDTA VYYCARDPAGSSVYTGGFNIWGQGTLVTVS SAS |
| 87 | VHV2 | EVQLVESGGGLVQPGGSLRLSCAASGFTLS SNAMCWVRQAPGKGLEWIGCIVYGNCYYAS WVNGRFTISSDNSKNTLYLQMNSLRAEDTA VYYCARDPAGSSVYTGGFNIWGQGTLVTVS SAS |
| 88 | VHV3 | EVQLVESGGGLVQPGGSLRLSCAASGFTLS SNAMSWVRQAPGKGLEWIGCIVYGNCYYAS WVNGRFTISSDNSKNTLYLQMNSLRAEDTA VYYCARDPAGSSVYTGGFNIWGQGTLVTVS SAS |
| 89 | VHV4 | EVQLVESGGGLVQPGGSLRLSCAASGFTLS SNAMSWVRQAPGKGLEWIGSIVYGNSYYAS WVNGRFTISSDNSKNTLYLQMNSLRAEDTA VYYCARDPAGSSVYTGGFNIWGQGTLVTVS SAS |
| 90 | VKV1 | DIQMTQSPSTLSASVGDRVTITCQASENIY SFLAWYQQKPGKAPKLLIYFASKLASGVPS RFSGSGSGTEFTLTISSLQPDDFATYYCQQ TVSYKNADTAFGGGTKVEIKRT |
| 91 | VKV2 | DIQMTQSPSTLSASVGDRVTITCQASENIY SFLAWYQQKPGKAPKLLIYFASKLASGVPS RFKGSGSGTEFTLTISSLQPDDFATYYCQQ TVSYKNADTAFGGGTKVEIKRT |
| 92 | VKV3 | DIQMTQSPSTLSASVGDRVTITCQASENIY SFLAWYQQKPGKAPKLLIYFASKLASGVPS RFSGSGSGTQFTLTISSLQPDDFATYYCQQ TVSYKNADTAFGGGTKVEIKRT |

TABLE 15-continued

Protein Sequences for Humanized
111H2 Variable Domain
(see Table 18 below for additional sequences)

| SEQ ID | Variant Names | Sequence |
|---|---|---|
| 93 | VKV4 | DIQMTQSPSTLSASVGDRVTITCQASENIY SFLAWYQQKPGKAPKLLIYFASKLASGVPS RFKGSGSGTQFTLTISSLQPDDFATYYCQQ TVSYKNADTAFGGGTKVEIKRT |

TABLE 16

Protein Sequences for Humanized
110H8 Variable Domains

| SEQ ID | Variant Names | Sequence |
|---|---|---|
| 94 | VHV1 | QVQLQESGPGLVKPSETLSLTCTVSGGSIS SVSISWIRQPPGKGLEWIGTIGASGSAYYA SWAKRRVTISVDTSKNQFSLKLSSVTAADT AVYYCAKEILYYGMDLWGQGTLVTVSSAS |
| 95 | VHV2 | QVQLQESGPGLVKPSETLSLTCTVSGGSIS SVSISWIRQPPGKGLEWIGTIGASGSAYYA SWAKRRVTISRDTSKNQFSLKLSSVTAADT AVYYCAKEILYYGMDLWGQGTLVTVSSAS |
| 96 | VHV3 | EVQLLESGGGLVQPGGSLRLSCAASGFTFS SVSISWVRQAPGKGLEWVSTIGASGSAYYA SWAKRRFTISRDNSKNTLYLQMNSLRAEDT AVYYCAKEILYYGMDLWGQGTLVTVSSAS |
| 97 | VHV4 | EVQLLESGGGLVQPGGSLRLSCTVSGIDLS SVSISWVRQAPGKGLEWVSTIGASGSAYYA SWAKRRFTISRDNSKNTLYLQMNSLRAEDT AVYYCAKEILYYGMDLWGQGTLVTVSSAS |
| 98 | VKV1 | DIQMTQSPSSLSASVGDRVTITCQASQSIS NYLAWYQQKPGKAPKLLIYAASNLEPGVPS RFSGSGSGTDFTLTISSLQPEDFATYYCQC TYGSTSSSDYGNAFGGGTKVEIKRT |
| 99 | VKV2 | DIQMTQSPSSLSASVGDRVTITCQASQSIS NYLAWYQQKPGKAPKLLIYAASNLEPGVPS RFSGSGSGTDFTLTISSLQPEDFATYYCQS TYGSTSSSDYGNAFGGGTKVEIKRT |
| 100 | VKV3 | DIQMTQSPSSLSASVGDRVTITCQASQSIS NYLAWYQQKPGKAPKLLIYAASNLEPGVPS RFSGSGSGTDYTLTISSLQPEDFATYYCQS TYGSTSSSDYGNAFGGGTKVEIKRT |
| 101 | VKV4 | DIQMTQSPSSLSASVGDRVTITCQASQSIS NYLAWYQQKPGKAPKLLIYAASNLEPGVPS RFSGSGSGTDYTLTISSLQPEDFATYYCQC TYGSTSSSDYGNAFGGGTKVEIKRT |
| 102 | VKV5 | DIQMTQSPSSLSASVGDRVTITCQASQSIS NYLAWYQQKPGKRPKLLIYAASNLEPGVPS RFSGSGSGTDYTLTISSLQPEDFATYYCQS TYGSTSSSDYGNAFGGGTKVEIKRT |
| 103 | VKV6 | DIQMTQSPSSLSASVGDRVTITCQASQSIS NYLAWYQQKPGKRPKLLIYAASNLEPGVPS RFSGSGSGTDYTLTISSLQPEDFATYYCQC TYGSTSSSDYGNAFGGGTKVEIKRT |
| 104 | VKV7 | DIQMTQSPSSLSASVGDRVTITCQASQSIS NYLAWYQQKPGKRPKLLIYAASNLEPGVPS RFSGSGSGTDFTLTISSLQPEDFATYYCQS TYGSTSSSDYGNAFGGGTKVEIKRT |

TABLE 17

DNA Sequences for Humanized Antibodies

| SEQ ID | Variant Names | Sequence |
|---|---|---|
| 105 | 116F3 HC | ATGGAATTGGGGCTGAGCTGGGTTTTCCTTG TTGCTATTTTAGAAGGTGTCCAGTGTGAGGT GCAGCTGTTGGAGTCTGGGGGAGGCTTGGTA CAGCCTGGGGGGTCCCTGAGACTCTCCTGTA CAGTCTCTGGATTCACCCTCAGTAGCATTTC GATAGGCTGGGTCCGCCAGGCTCCAGGGAAG GGGCTGGAGTGGGTCTCAACCATTAGTGACA GTGGTAGCGCATACTACGCGAGCTGGGCGAA AAGCCGGTTCACCATCTCCAGAGACAATTCC AAGAACACGCTGTATCTGCAAATGAACAGCC TGAGAGCCGAGGACACGGCCGTATATTACTG TGCGAAAGAAATCCTTTACTACGGCATGGAC CTCTGGGGCCAGGGCACCCTGGTCACCGTCT CCTCAGCTAGCACCAAGGGCCCATCGGTCTT CCCCCTGGCGCCCTGCTCCAGGAGCACCTCC GAGAGCACAGCCGCCCTGGGCTGCCTGGTCA AGGACTACTTCCCCGAACCGGTGACGGTGTC GTGGAACTCAGGCGCCCTGACCAGCGGCGTG CACACCTTCCCGGCTGTCCTACAGTCCTCAG GACTCTACTCCCTCAGCAGCGTGGTGACCGT GCCCTCCAGCAGCTTGGGCACGAAGACCTAC ACCTGCAACGTAGATCACAAGCCCAGCAACA CCAAGGTGGACAAGAGAGTTGAGTCCAAATA TGGTCCCCCATGCCCACCATGCCCAGCACCT GAGTTCCTGGGGGGACCATCAGTCTTCCTGT TCCCCCCAAAACCCAAGGACACTCTCATGAT CTCCCGGACCCCTGAGGTCACGTGCGTGGTG GTGGACGTGAGCCAGGAAGACCCCGAGGTCC AGTTCAACTGGTACGTGGATGGCGTGGAGGT GCATAATGCCAAGACAAAGCCGCGGGAGGAG CAGTTCAACAGCACGTACCGTGTGGTCAGCG TCCTCACCGTCCTGCACCAGGACTGGCTGAA CGGCAAGGAGTACAAGTGCAAGGTCTCCAAC AAAGGCCTCCCGTCCTCCATCGAGAAAACCA TCTCCAAAGCCAAAGGGCAGCCCCGAGAGCC ACAGGTGTACACCCTGCCCCCATCCCAGGAG GAGATGACCAAGAACCAGGTCAGCCTGACCT GCCTGGTCAAAGGCTTCTACCCCAGCGACAT CGCCGTGGAGTGGGAGAGCAATGGGCAGCCG GAGAACAACTACAAGACCACGCCTCCCGTGC TGGACTCCGACGGCTCCTTCTTCCTCTACAG CAGGCTCACCGTGGACAAGAGCAGGTGGCAG GAGGGGAATGTCTTCTCATGCTCCGTGATGC ATGAGGCTCTGCACAACCACTACACACAGAA GAGCCTCTCCCTGTCTCCGGGTAAATGA |
| 106 | 116F3 LC | ATGGACATGAGGGTCCCCGCTCAGCTCCTGG GGCTCCTGCTACTCTGGCTCCGAGGTGCCAG ATGTGACATCCAGATGACCCAGTCTCCATCC TCCCTGTCTGCATCTGTAGGAGACAGAGTCA CCATCACTTGCCAGGCCAGTGAGGACATTGA AAGCTATTTAGCCTGGTATCAGCAGAAACCA GGGAAAGCCCCTAAGCTCCTGATCTATGCTG CATCCAATCTGGAGCCTGGGGTCCCATCAAG GTTCAGTGGCAGTGGATCTGGGACAGATTTC ACTCTCACCATCAGCAGTCTGCAACCTGAAG ATTTTGCAACTTACTACTGTCAAGCTACTTA TGGTAGTACTAGTAGTAGTGATTATGGTAAT GCTTTCGGCGGAGGGACCAAGGTGGAAATCA AACGTACGGTGGCTGCACCATCTGTCTTCAT CTTCCCGCCATCTGATGAGCAGTTGAAATCT GGAACTGCCTCTGTTGTGTGCCTGCTGAATA ACTTCTATCCCAGAGAGGCCAAAGTACAGTG GAAGGTGGATAACGCCCTCCAATCGGGTAAC TCCCAGGAGAGTGTCACAGAGCAGGACAGCA AGGACAGCACCTACAGCCTCAGCAGCACCCT GACGCTGAGCAAAGCAGACTACGAGAAACAC AAAGTCTACGCCTGCGAAGTCACCCATCAGG GCCTGAGTTCGCCCGTCACAAAGAGCTTCAA CAGGGGAGAGTGTTAG |
| 107 | 111H2 HC | ATGGAACTTGGACTGTCTTGGGTGTTTCTTG TCGCTATCCTGGAAGGAGTGCAATGCGAAGT GCAGCTGGTCGAAAGCGGAGGCGGACTGGTC CAACCTGGCGGATCCCTGAGACTGTCCTGTG |

TABLE 17-continued

DNA Sequences for Humanized Antibodies

| SEQ ID | Variant Names | Sequence |
|---|---|---|
| | | CCGCCTCCGGTTTTACCCTGAGCAGCAACGC CATGTCCTGGGTCAGACAGGCACCAGGAAAA GGGCTGGAGTGGATCGGTTGCATTGTGTACG GGAATTGCTACTACGCCAGCTGGGTGAACGG ACGGTTCACCATCAGCTCAGATAATTCAAAG AACACCCTTTACCTCCAAATGAACTCCCTGC GCGCAGAGGATACTGCCGTGTACTACTGCGC CAGGGATCCTGCCGGATCGTCGGTCTACACC GGGGGCTTCAACATCTGGGGTCAAGGCACCC TCGTGACCGTGAGCTCTGCGTCGACCAAGGG CCCGTCCGTGTTCCCGCTGGCCCCATGCTCA CGCTCGACCTCCGAGTCCACAGCCGCACTGG GCTGCTTGGTCAAAGACTACTTCCCTGAACC CGTCACTGTGTCGTGGAACAGCGGGGCTCTC ACCAGCGGCGTGCATACCTTTCCGGCGGTGC TTCAGAGCTCCGGACTGTACTCCCTCTCGTC CGTCGTGACTGTCCCCTCCTCGTCCCTGGGC ACCAAGACCTACACTTGCAATGTGGACCACA AGCCCTCGAACACCAAAGTGGACAAGCGGGT GGAGTCGAAGTATGGCCCATGCCCTCCT TGTCCTGCGCCCGAGTTTCTGGGAGGGCCAT CCGTGTTCCTCTTCCCGCCGAAGCCGAAGGA CACCCTGATGATTTCCCGCACTCCTGAAGTG ACCTGTGTGGTGGTGGACGTGTCCCAGGAAG ATCCGGAAGTGCAGTTCAATTGGTATGTGGA CGGAGTCGAGGTGCACAACGCAAAGACTAAG CCTAGGGAGGAACAGTTCAACTCCACCTACC GCGTGGTGTCAGTGCTGACGGTGCTGCACCA GGACTGGTTGAACGGCAAAGAGTACAAGTGC AAGGTGTCCAACAAGGGACTGCCGTCCAGCA TCGAAAAGACCATCTCCAAGGCCAAGGGACA GCCCAGAGAACCGCAAGTGTACACCCTCCCG CCAAGCCAGGAGGAAGAGATGACCAAGAACCAAG TGTCCCTGACTTGCCTCGTGAAGGGATTCTA CCCCTCCGACATCGCCGTGGAATGGGAATCA AATGGACAGCCCGAAAACAACTACAAGACCA CGCCGCCTGTGCTGGACTCGGACGGTTCCTT CTTCCTGTACTCCCGCCTCACCGTCGATAAG TCACGGTGGCAGGAGGGAACGTGTTCAGCT GCTCCGTCATGCACGAAGCGCTCCACAACCA TTATACTCAGAAGTCCCTGTCCTTGTCCCCC GGAAAG |
| 108 | 111H2 LC | ATGGATATGAGAGTGCCTGCCCAACTCCTCG GACTTCTGCTGCTTTGGTTGAGAGGTGCCAG ATGCGATATCCAAATGACCCAGTCACCGTCC ACCCTGAGCGCCTCTGTGGGCGACCGCGTCA CTATCACTTGCCAAGCCTCGGAGAACATCTA TTCTTCCTGGCCTGGTACCAGCAGAAACCG GGGAAGGCTCCTAAGCTGCTCATCTACTTCG CGTCCAAGCTGGCCTCCGGAGTGCCATCACG GTTCTCTGGAAGCGGGAGCGGAACCCAGTTC ACCCTGACTATTAGCTCCTTGCAACCCGACG ACTTCGCGACCTACTACTGTCAGCAGACCGT GTCCTACAAGAACGCGGATACAGCCTTTGGT GGCGGGACTAAGGTCGAAATTAAGCGTACGG TGGCTGCTCCATCCGTGTTCATCTTCCCGCC TTCCGACGAGCAGCTGAAGTCCGGTACCGCA AGCGTGGTCTGCCTGCTCAACAACTTCTACC CCCGCGAAGCCAAGGTCCAGTGGAAGGTGGA CAACGCACTCCAGTCGGGGAATTCACAGGAA AGCGTGACTGAGCAGGACTCCAAGGACTCGA CCTACTCGCTGTCCTCCACCCTGACTCTGTC CAAGGCCGACTACGAAAAGCACAAGGTCTAT GCCTGTGAAGTGACCCACCAGGGACTTTCCA GCCCCGTGACGAAATCCTTCAACCGGGGAGA GTGC |
| 109 | 111H2 HC V1.5 | ATGGAGTTCTGGTTGTCCTGGGTGTTCCTCG TCGCTATTCTTAAGGGAGTGCAGTGTGAAGT GCAGCTTGTCGAGTCCGGCGGCGGGACTCGTG CAGCCCGGCGGAAGCCTGAGACTCTCCTGCG CCGCCTCGGGATTCGACCTCTCATCCAACGC CATGTGCTGGGTCCGACAGGCCCCGGGGAAG GGTCTGGAGTGGATCGGTTGCATTGTGTACG GAAACTTCTACTACGCGTCCTGGGTCAAGGG CCGGTTCACCATTTCCACCGATAACGCCAAG AACTCCCTCTACCTCCAAATGAACAGCCTGA GGGCTGAGGACACTGCGGTGTACTTTTGCGC CCGGGATCCCGCCGGGTCCTCCGTGTACACT GGAGGGTTCAACATCTGGGGCCAGGGTACCC TCGTGACTGTCAGCAGCGCTAGCACTAAGGG GCCCTCCGTGTTCCCCCTGGCGCCTTGTTCC CGCTCCACCTCTGAATCCACCGCTGCCCTGG GCTGCCTCGTGAAGGACTACTTCCCTGAACC GGTCACTGTGTCCTGGAACTCCGGAGCCTTG ACTTCGGGTGTCCACACTTTTCCCGCCGTGC TGCAATCAAGCGGTCTGTACTCCCTGAGCTC GGTCGTGACTGTGCCCAGCTCGTCGCTCGGA ACCAAGACCTACACGTGCAACGTCGACCACA AGCCGTCGAACACGAAGGTCGATAAGCGCGT GGAGTCCAAATACGGACCCCCTTGTCCGCCA TGCCCAGCCCCCGAATTCCTGGGCGGCCCCA GCGTGTTCCTGTTCCCGCCTAAACCGAAGGA CACTCTGATGATCAGCCGGACCCCCGAAGTG ACATGCGTGGTGGTGGACGTGTCCCAGGAAG ATCCAGAAGTCCAGTTCAATTGGTACGTCGA CGGCGTGGAAGTGCACAACGCAAAGACCAAG CCCCGCGAGGAACAGTTCAATTCCACCTACC GCGTGGTGTCCGTGCTGACCGTGCTGCATCA GGACTGGCTGAACGGAAAGGAGTACAAATGC AAAGTGTCCAACAAGGGACTGCCTTCAAGCA TTGAAAAGACCATCTCCAAGGCCAAGGGGCA GCCTAGAGAGCCACAAGTGTACACCCTGCCC CCTTCACAAGAGGAAATGACCAAGAACCAAG TGTCGCTGACCTGTCTGGTCAAGGGATTCTA CCCGAGCGATATCGCAGTGGAATGGGAGAGC AATGGCCAGCCTGAGAACAACTACAAGACCA CCCCGCCGGTGCTCGACTCCGACGGTTCATT TTTCTTGTATTCCCGGCTGACTGTGGACAAG TCACGGTGGCAGGAGGGCAACGTGTTCTCCT GCTCCGTGATGCATGAAGCCCTGCACAACCA CTATACCCAGAAGTCGCTGTCCCTGTCGTTG GGGAAGTGA |
| 110 | 111H2 LC V1.5 | ATGGATATGCGCGTGCTTGCCCAACTGCTCG GACTCCTTCTGCTCTGCTTTCCCGGTGCTAG ATGCGACATCCAGATGACTCAGAGCCCTTCC TCCCTGTCCGCCTCCGTGGGCGATAGGGTCA CAATTACTTGTCAAGCCTCCGAAAACATCTA TAGCTTCCTCGCGTGGTACCAGCAGAAGCCA GGAAAGAGCCCCAAGCCGCTGATCTATTTCG CGTCTAAGTTGGCCTCCGGAGTGCCGTCCCG GTTCTCGGGATCAGGTTCAGGGACTGACTTC ACTCTGACCATTAGCTCGCTGCAACCCGAAG ATTTCGCCACCTACTACTGCCAGCAAACCGT GTCCTACAAGAACGCCGACACTGCGTTCGGC CAGGGCACCAAAGTGGAGATCAAGCGTACGG TGGCCGCCCGTCCGTGTTCATCTTTCCGGCC TTCCGACGAACAGCTGAAGTCGGGAACCGCA TCCGTCGTGTGCCTGCTGAACAACTTCTACC CACGCGAAGCTAAAGTCAGTGGAAAGTGGA TAATGCACTGCAGTCCGGAAACTCGCAGGAG AGCGTGACCGAGCAGGACTCAAAGGACTCCA CTTACTCCCTGTCGTCCACCCTGACGTTGAG CAAGGCCGACTACGAGAAGCACAAGGTCTAC GCCTGCGAAGTGACCCATCAGGGCCTGAGCT CGCCCGTCACCAAGTCATTCAACCGGGGGGA GTGTTGA |

TABLE 18

Additional Protein Sequences for
Humanized 111H2 Variable Domain

| SEQ ID | Variant Names | Sequence |
|---|---|---|
| 111 | VHV5 | EVQLVESGGGLVQPGGSLRLSCAASGFDLS SNAMCWVRQAPGKGLEWIGCIVYGNCYYAS WVKGRFTISTDNAKNSLYLQMNSLRAEDTA VYFCARDPAGSSVYTGGFNIWGQGTLVTVS SAS |
| 112 | VHV6 | EVQLVESGGGLVQPGGSLRLSCAASGFDLS SNAMCWVRQAPGKGLEWIGCIVYGNFYYAS WVKGRFTISTDNAKNSLYLQMNSLRAEDTA VYFCARDPAGSSVYTGGFNIWGQGTLVTVS SAS |
| 113 | VKV5 | DIQMTQSPSSLSASVGDRVTITCQASENIY SFLAWYQQKPGKSPKPLIYFASKLASGVPS RFSGSGSGTDFTLTISSLQPEDFATYYCQQ TVSYKNADTAFGQGTKVEIKRT |

TABLE 19

Protein Sequences for a
Humanized 111H2 Antibody ASKB1296

| SEQ ID | Names | Sequence |
|---|---|---|
| 114 | HC V1.5 | EVQLVESGGG LVQPGGSLPL SCAASGFDLS SNAMCWVRQA PGKGLEWIGC IVYGNFYYAS WVKGRFTIST DNAKNSLYLQ MNSLRAEDTA VYFCARDPAG SSVYTGGFNI WGQGTLVTVS SASTKGPSVF PLAPCSRSTS ESTAALGCLV KDYFPEPVTV SWNSGALTSG VHTFPAVLQS SGLYSLSSVV TVPSSSLGTK TYTCNVDHKP SNTKVDKPVE SKYGPPCPPC PAPEFLGGPS VFLFPPKPKD TLMISRTPEV TCVVVDVSQE DPEVQFNWYV DGVEVHNAKT KPPEEQFNST YRVVSVLTVL HQDWLNGKEY KCKVSNKGLP SSIEKTISKA KGQPPEPQVY TLPPSQEEMT KNQVSLTCLV KGFYPSDIAV EWESNGQPEN NYKTTPPVLD SLGSFFLYSR LTVDKSRWQE GNVFSCSVMH EALHNHYTQK SLSLSLGK |
| 115 | LC V1.5 | DIQMTQSPSS LSASVGDRVT ITCQASENIY SFLAWYQQKP GKSPKPLIYF ASKLASGVPS RFSGSGSGTD FTLTISSLQP EDFATYYCQQ TVSYKNADTA FGQGTKVEIK RTVAAPSVFI FPPSDEQLKS GTASVVCLLN NFYPREAKVQ NKVDNALQSG NSQESVTEQD SKDSTYSLSS TLTLSKADYE KHKVYACEVT HQGLSSPVTK SFNRGEC |

Cell Line Development

For the cell line development for stable expression, CHOZN-GS-/- cells and pCGS3 expression vector from Sigma were used. DNA sequences encoding the genes of the humanized antibody 111H2 V1.5, were cloned into the pCGS3 expression vectors. These DNA constructs then were linearized and introduced into CHOZN-GS-/- cells by electroporation. The transfected cells were selected by medium without L-glutamine. The survived cells were subcloned by ClonePix or limiting dilution and analyzed for the protein expression levels using ELISA or Bio-Layer Interferometry technology.

Production of Humanized Antibody

For transient expression, expression plasmid constructs containing DNA sequences encoding the genes of the humanized antibody 111H2 V1.5, were introduced into HEK-293 cells transiently by using polyethylenimine (PEI). The transfected cells were treated by alproic acid (VPA) 24 hours post transfection to enhance protein expression. The supernatants were harvested on day 6 and the antibodies were purified.

For expression with stable cell line or cell pools, the cells were seeded at approximately 0.5 million per ml in the 1 L bioreactors. The cells were fed and cultured for approximately 10-14 days. The supernatants were harvested and the antibodies were purified.

The purification of the humanized antibody involved the Protein A affinity column followed by an anion exchange chromatography operated in the flow-through mode. It was further followed by a mixed mode chromatography. The purified antibody was formulated in a formulation containing 10 mM Acetic acid, 7% sucrose, 0.01% polysorbate-80, pH of approximately 5. It was stored at 2-8° C. or −80° C. until use.

Figure 10:
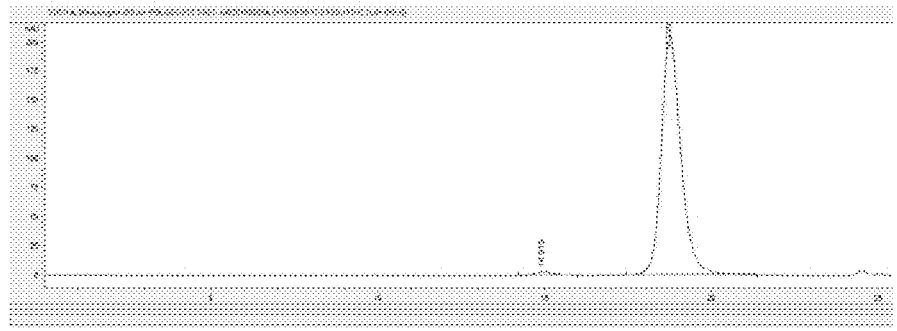
FIG. 10: SEC-HPLC for the purity of the humanized PD-L1 antibody 111H2.
Figure 11:
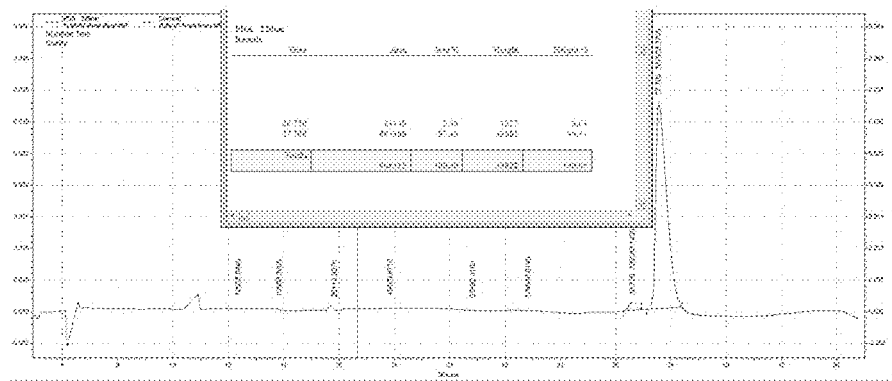
FIG. 11: CE-SDS (NR) for the purity of the humanized PD-L1 111H2.
Figure 12:
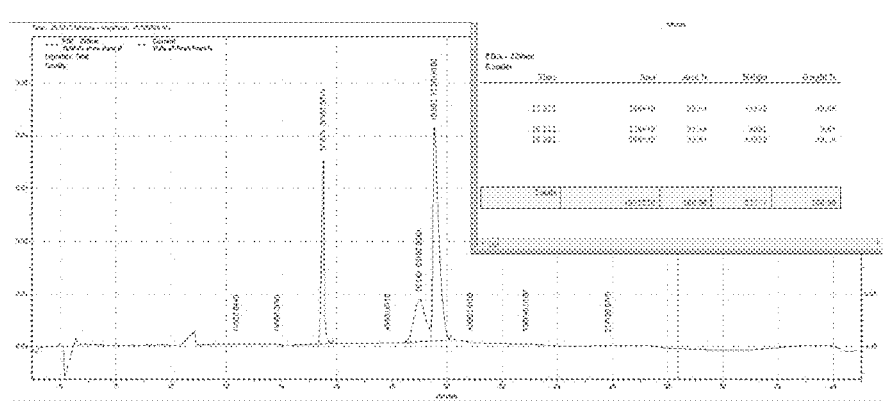
FIG. 12: CE-SDS (R) for the purity of the humanized PD-L1 111H2.

The purities of the antibody were assessed by HPLC analysis such as SEC-HPLC (FIG. 10) and CE-SDS analysis (FIG. 11 and FIG. 12).

Animal Efficacy Study

Figure 13A:
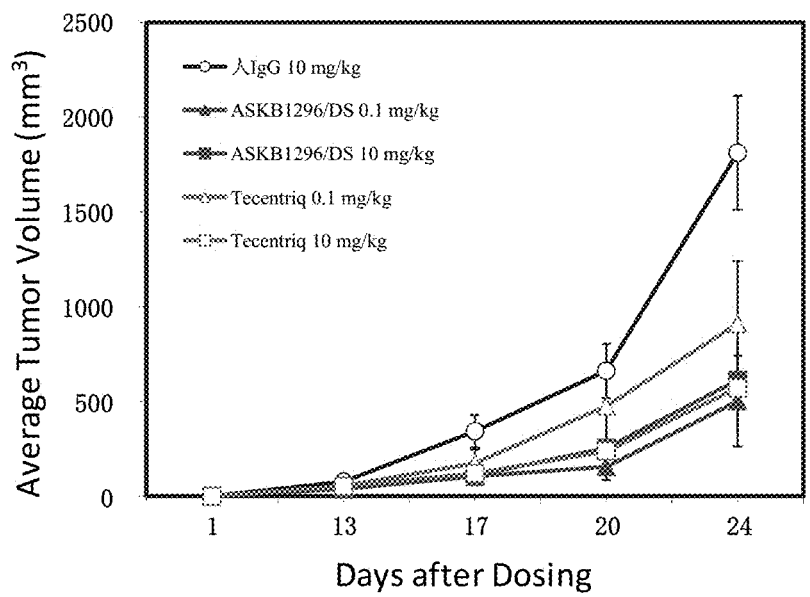
FIG. 13A. Animal efficacy study of the humanized PD-L1 antibody ASKB1296.
Figure 13B:
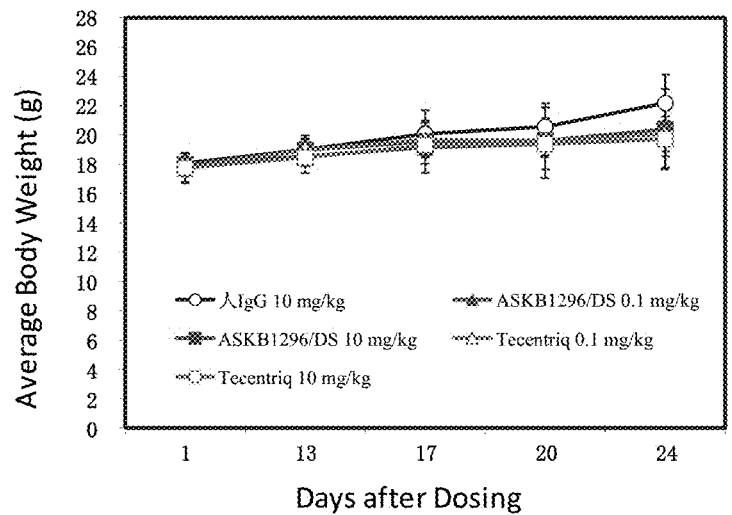
FIG. 13B. Impacts of PD-L1 antibodies on mouse body weight.

C67BL/6 mice transplanted with colon cancer cell line MC-38 were used to evaluate the efficacy of PD-L1 antibody ASKB1296 in comparison with the marketed PD-L1 antibody Tecetriq (positive control). The cancer cells were transplanted subcutaneously on Day 0. The dosing of PD-L1 antibodies or negative control human IgG were started on Day 1. The dosages and dosing frequency are listed on Table 20. The inhibition of the tumor formation and the sizes of the tumors formed were measured to assess the efficacy of the PD-L1 antibodies. The results are shown in FIG. 13A. The data indicated that ASKB1296 had comparable or better efficacy in the inhibition of the tumor formation than the positive control. The effects of the PD-L1 antibodies on the mouse body weight were similar between ASKB1296 and the positive control.

TABLE 20

Animal study groups, dosages and dosing schedule.

| Tumor | Antibody | Number of Animals | Dose (mg/kg) | Administration Route | Dosing Frequency |
|---|---|---|---|---|---|
| MC-38/ H-11 | Control Human IgG | 10 | 10 | IP | Q2D × 10 |
| | PD-L1 Antibody ASKB1296 | 10 | 0.1 | IP | Q2D × 10 |
| | PD-L1 Antibody ASKB1296 | 10 | 10 | IP | Q2D × 10 |
| | Tecentriq ® | 10 | 0.1 | IP | Q2D × 10 |
| | Tecentriq ® | 10 | 10 | IP | Q2D × 10 |

The non-limiting examples described above are provided for illustrative purposes only in order to facilitate a more complete understanding of the disclosed subject matter. These examples should not be construed to limit any of the embodiments described in the present specification, including those pertaining to the antibodies, pharmaceutical compositions, or methods and uses for treating cancer, a neurodegenerative or an infectious disease.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:
1. An antibody which binds to human PD-L1 protein, the antibody selected from the group consisting of:
   (1) an antibody comprising a heavy chain variable region comprising heavy chain CDR1 having the amino acid sequence as set forth in SEQ ID NO: 19, heavy chain CDR2 having the amino acid sequence as set forth in SEQ ID NO: 20, and heavy chain CDR3 having the amino acid sequence as set forth in SEQ ID NO: 21, and a light chain variable region comprising light chain CDR1 having the amino acid sequence as set forth in SEQ ID NO: 22, light chain CDR2 having the amino acid sequence as set forth in SEQ ID NO: 23, and light chain CDR3 having the amino acid sequence as set forth in SEQ ID NO: 24;
   (2) an antibody comprising a heavy chain variable region comprising heavy chain CDR1 having the amino acid sequence as set forth in SEQ ID NO: 25, heavy chain CDR2 having the amino acid sequence as set forth in SEQ ID NO: 26, and heavy chain CDR3 having the amino acid sequence as set forth in SEQ ID NO: 27, and a light chain variable region comprising light chain CDR1 having the amino acid sequence as set forth in SEQ ID NO: 28, light chain CDR2 having the amino acid sequence as set forth in SEQ ID NO: 29, and light chain CDR3 having the amino acid sequence as set forth in SEQ ID NO: 30;
   (3) an antibody comprising a heavy chain variable region comprising heavy chain CDR1 having the amino acid sequence as set forth in SEQ ID NO: 31, heavy chain CDR2 having the amino acid sequence as set forth in SEQ ID NO: 32, and heavy chain CDR3 having the amino acid sequence as set forth in SEQ ID NO: 33, and a light chain variable region comprising light chain CDR1 having the amino acid sequence as set forth in SEQ ID NO: 34, light chain CDR2 having the amino acid sequence as set forth in SEQ ID NO: 35, and light chain CDR3 having the amino acid sequence as set forth in SEQ ID NO: 36;
   (4) an antibody comprising a heavy chain variable region comprising heavy chain CDR1 having the amino acid sequence as set forth in SEQ ID NO: 37, heavy chain CDR2 having the amino acid sequence as set forth in SEQ ID NO: 38, and heavy chain CDR3 having the amino acid sequence as set forth in SEQ ID NO: 39, and a light chain variable region comprising light chain CDR1 having the amino acid sequence as set forth in SEQ ID NO: 40, light chain CDR2 having the amino acid sequence as set forth in SEQ ID NO: 41, and light chain CDR3 having the amino acid sequence as set forth in SEQ ID NO: 42;
   (5) an antibody comprising a heavy chain variable region comprising heavy chain CDR1 having the amino acid sequence as set forth in SEQ ID NO: 43, heavy chain CDR2 having the amino acid sequence as set forth in SEQ ID NO: 44, and heavy chain CDR3 having the amino acid sequence as set forth in SEQ ID NO: 45, and a light chain variable region comprising light chain CDR1 having the amino acid sequence as set forth in SEQ ID NO: 46, light chain CDR2 having the amino acid sequence as set forth in SEQ ID NO: 47, and light chain CDR3 having the amino acid sequence as set forth in SEQ ID NO: 48;
   (6) an antibody comprising a heavy chain variable region comprising heavy chain CDR1 having the amino acid sequence as set forth in SEQ ID NO: 49, heavy chain CDR2 having the amino acid sequence as set forth in SEQ ID NO: 50, and heavy chain CDR3 having the amino acid sequence as set forth in SEQ ID NO: 51, and a light chain variable region comprising light chain CDR1 having the amino acid sequence as set forth in SEQ ID NO: 52, light chain CDR2 having the amino acid sequence as set forth in SEQ ID NO: 53, and light chain CDR3 having the amino acid sequence as set forth in SEQ ID NO: 54;
   (7) an antibody comprising a heavy chain variable region comprising heavy chain CDR1 having the amino acid sequence as set forth in SEQ ID NO: 55, heavy chain CDR2 having the amino acid sequence as set forth in SEQ ID NO: 56, and heavy chain CDR3 having the amino acid sequence as set forth in SEQ ID NO: 57, and a light chain variable region comprising light chain CDR1 having the amino acid sequence as set forth in SEQ ID NO: 58, light chain CDR2 having the amino acid sequence as set forth in SEQ ID NO: 59, and light chain CDR3 having the amino acid sequence as set forth in SEQ ID NO: 60;
   (8) an antibody comprising a heavy chain variable region comprising heavy chain CDR1 having the amino acid sequence as set forth in SEQ ID NO: 61, heavy chain CDR2 having the amino acid sequence as set forth in SEQ ID NO: 62, and heavy chain CDR3 having the amino acid sequence as set forth in SEQ ID NO: 63, and a light chain variable region comprising light chain CDR1 having the amino acid sequence as set forth in SEQ ID NO: 64, light chain CDR2 having the amino acid sequence as set forth in SEQ ID NO: 65, and light chain CDR3 having the amino acid sequence as set forth in SEQ ID NO: 66; and
   (9) an antibody comprising a heavy chain variable region comprising heavy chain CDR1 having the amino acid sequence as set forth in SEQ ID NO: 67, heavy chain CDR2 having the amino acid sequence as set forth in SEQ ID NO: 68, and heavy chain CDR3 having the amino acid sequence as set forth in SEQ ID NO: 69, and a light chain variable region comprising light chain CDR1 having the amino acid sequence as set forth in SEQ ID NO: 70, light chain CDR2 having the amino acid sequence as set forth in SEQ ID NO: 71, and light chain CDR3 having the amino acid sequence as set forth in SEQ ID NO: 72.

2. The antibody of claim 1 which binds to human PD-L1 protein, further comprising a heavy chain variable domain selected from the group consisting of SEQ ID NO: 1, 2, 3, 4, 5, 6, 7, 8, and 9.

3. The antibody of claim 1 which binds to human PD-L1 protein, further comprising a light chain variable domain selected from the group consisting of SEQ ID NO: 10, 11, 12, 13, 14, 15, 16, 17 and 18.

4. An antibody according to any one of claim 1, 2 or 3, wherein the antibody is humanized.

5. A humanized antibody which binds to human PD-L1 protein comprising a heavy chain variable domain selected from the group consisting of SEQ ID NO: 73, 74, 75, 76, 77, 80, 81, 82, 83, 84, 86, 87, 88, 89, 94, 95, 96, 97, 111 and 112.

6. The antibody of claim 1 which binds to human PD-L1 protein, wherein the antibody is humanized and comprises a light chain variable domain selected from the group consisting of SEQ ID NO: 78, 79, 85, 90, 91, 92, 93, 98, 99, 100, 101, 102, 103, 104 and 113.

7. The antibody of claim 1 which binds to human PD-L1 protein, wherein the antibody is humanized and comprises a heavy chain variable domain having the amino acid sequence as set forth in SEQ ID NO: 115.

8. The PD-L1 antibody of claim 7, wherein the antibody is bispecific and further comprises one or more binding domains which bind to human TGF-Beta, TIGIT, LAG3, TIM3, CD39, or CD73.

9. A nucleic acid sequence which encodes a humanized human PD-L1 antibody heavy chain selected from the group consisting of SEQ ID NO: 105; SEQ ID NO: 107; and SEQ ID NO: 109.

10. A nucleic acid sequence which encodes a humanized human PD-L1 antibody light chain selected from the group consisting of SEQ ID NO: 106; SEQ ID NO: 108; and SEQ ID NO: 110.

11. A pharmaceutical composition comprising an antibody according to claim 1.

12. A method of treating cancer, the method comprising the step of administering a pharmaceutical composition comprising an antibody according to claim 1 to a subject in need thereof, wherein the subject in need thereof has a cancer associated with expression of the human PD-L1 protein at a predetermined threshold value and the cancer is selected from the group consisting of kidney, breast, lung, kidney, bladder, urinary tract, urethra, penis, vulva, vagina, cervical, colon, ovarian, prostate, pancreas, stomach, brain, head and neck, skin, uterine, testicular, esophagus, and liver cancer.

13. A method of treating a neurodegenerative disease, the method comprising the step of administering a pharmaceutical composition of claim 1 to a subject in need thereof having a neurodegenerative disease associated with the expression of the human PD-L1 protein at a predetermined threshold value, wherein the neurodegenerative disease is selected from the group consisting of amyotrophic lateral sclerosis, Parkinson's disease, Alzheimer's disease, Huntington's chorea, frontotemporal dementia, vascular dementia, mild cognitive impairment, stroke, and focal ischemia associated dementia.

14. The method of claim 13, wherein the neurodegenerative disease is Alzheimer's disease.

* * * * *